US006245758B1

(12) United States Patent
Stern et al.

(10) Patent No.: US 6,245,758 B1
(45) Date of Patent: Jun. 12, 2001

(54) METHODS OF USE FOR PEROXYNITRITE DECOMPOSITION CATALYSTS, PHARMACEUTICAL COMPOSITIONS THEREFOR

(76) Inventors: Michael K. Stern, 1075 Wilson Ave., University City, MO (US) 63130; Daniela Salvemini, 1651 Timber Ridge Estates Dr., Ballwin, MO (US) 63011

( * ) Notice: Subject to any disclaimer, the term of this patent is extended or adjusted under 35 U.S.C. 154(b) by 0 days.

(21) Appl. No.: 08/709,788

(22) Filed: Sep. 9, 1996

Related U.S. Application Data

(63) Continuation of application No. 08/431,593, filed on May 1, 1995, which is a continuation-in-part of application No. 08/242,498, filed on May 13, 1994, now abandoned.

(51) Int. Cl.[7] ........................ A61K 31/40; A61K 31/295; A61K 31/555

(52) U.S. Cl. .................. 514/185; 540/145; 540/470; 540/122; 514/461; 514/184; 514/501; 514/502

(58) Field of Search .................................... 514/501, 502, 514/184, 185; 540/145, 122, 470

(56) References Cited

U.S. PATENT DOCUMENTS

| | | |
|---|---|---|
| 4,866,054 | 9/1989 | Dori et al. ............................. 514/184 |
| 5,277,908 | 1/1994 | Beckman et al. .................... 424/94.4 |
| 5,284,647 | 2/1994 | Niedballa et al. ...................... 424/81 |

FOREIGN PATENT DOCUMENTS

| | | |
|---|---|---|
| 0 210 351 A2 | 2/1987 | (EP) . |
| 0 484 027 A1 | 5/1992 | (EP) . |
| 9287097 | 7/1992 | (EP) . |
| 0 524 161 A1 | 1/1993 | (EP) . |
| 0 525 938 A1 | 2/1993 | (EP) . |
| 5331063 | 12/1993 | (JP) . |
| WO 87/04071 | 5/1987 | (WO) . |
| WO 89/02269 | 3/1989 | (WO) . |
| WO 92/08482 | 5/1992 | (WO) . |
| WO 93/10777 PCT/US93/ | 6/1993 | (WO) . |
| 01288 | 9/1993 | (WO) . |
| WO 93/16721 | 9/1993 | (WO) . |
| WO 94/26263 | 5/1994 | (WO) . |
| WO 94/13300 | 6/1994 | (WO) . |
| WO 94/15925 | 7/1994 | (WO) . |
| WO 95/05814 | 3/1995 | (WO) . |

OTHER PUBLICATIONS

CRC Handbook, 68th Ed. (CRC Press, Boca Raton, 1987), reprinting IUPAC Nomenclature Rule 7.322, p. B–61.
Cotton and Wilkinson *Advanced Inorganic Chemistry*, 5th edition, pp. 481–482, 1988.
Latos–Grazynski and Lisowski *J. Am. Chem. Soc.*, 1987, 109, 4428–4429.
Lesht and Bauman, Jr. *Inorganic Chemistry*, vol. 17, No. 12 (1978), 3332–4.
Crutchley and Powell *Inorganica Chim. Acta*, 24 (1977) L15–L16.
Baxter et al. *Inorg. Chem.* 1995, 34, 2795–6.
119:203240b, vol. 119—(1993)—p. 875—26–Biomolecules—Preparation of Porphyrin Transition Metal Compounds as Hypoglycemics.
Anticancer Research 14: 2717–1726 (1994) "Scavenging Effects of Hemoglobin and Related Heme Containing Compounds on Nitric Oxide, Reactive Oxidants and Carcinogenic Volatile Nitrosocompounds of Cigarette Smoke. A New Method for Protection against the Dangerous Cigarette Constituents", George Deliconstantinos, et al.
Archives of Biochemistry and Biophysics, vol. 288, No. 2, Aug. 1, pp. 481–487, (1991) "Peroxynitrite–Induced Membrane Lipid Peroxidation: The Cytotoxic Potential of Superoxie and Nitric Oxide", Rafael Radi, et al.
Hibbs et al, Science, 1987, 235, 473–476.
Rimele et al, J. Pharmacol. Exp. Ther., 1988, 245, 102–111.
Curran et al, J. Exp. Med., 1989, 170, 1769–1774.
Monocada et al, Pharmacology, 1991, 43, 109–142.
Absts. of 1st Annual Mtg. of Oxygen Society, Nov. 12–14, 1993, Charleston,SC, "Nitric Oxide Requires Superoxide to Exert Bactericidal Activity", by L. Brunnelli and J.S. Beckmann.
Beckman et al, "Apparent Hydroxyl Radical Production by Peroxynitrite: Implications for Endothelial Injury from Nitric Oxide and Superoxide" in Proc.Natl.Acad.Sci.USA, vol. 87,pp. 1620–1624, Feb. 1990.
Radi et al, "Peroxynitrite Oxidation of Sulfhydryls" in the Journal of Biological Chemistry, vol. 266, No. 7, Mar. 5, 1991, pp. 4244–4250.
Hardy et al, Abs. "Experimental Biology" section of FASEB on Mar. 28–Apr. 1, 1993 in New Orleans, LA.
Radi et al, Arch. Biochem. Biophys, 1991, 288, 481–487.
Rachmilewitz et al in "Peroxynitrite–induced Rat Colitis: A New Model of Colonic Inflammation" from Gastroenterology 105 (6)1993, pp. 1681–1688.
Beckman et al, "ALS–SOD and Peroxynitrite" (Scientific Correspondence)) in Nature, vol. 364, Aug. 12, 1993.
Hogg et al, "Peroxynitrite and Atherosclerosis", Biochemical Society Transactions, vol. 21.

(List continued on next page.)

*Primary Examiner*—Richard L. Raymond
*Assistant Examiner*—Pavanaram K Sripada
(74) *Attorney, Agent, or Firm*—Monsanto Company

(57) ABSTRACT

The present invention provides a method for the treatment of diseases by the decomposition of peroxynitrite, preferably decomposition to benign products, comprising the use of a complex which is a selected ligand structure providing a complexed metal such as Mn, Fe, Ni and V transition metals. The method of use, as well as novel pharmaceutical compositions therefor, are for the treatment of diseases advantageously affected by decomposition of peroxynitrite ed at a rate over the natural background rate of decay of peroxynitrite in humans suffering from the disease which comprises administration of an amount of a complex, in dosage unit form, which is effective for such acceleration of the decomposition of peroxynitrite .

22 Claims, 10 Drawing Sheets

OTHER PUBLICATIONS

Figure 1:
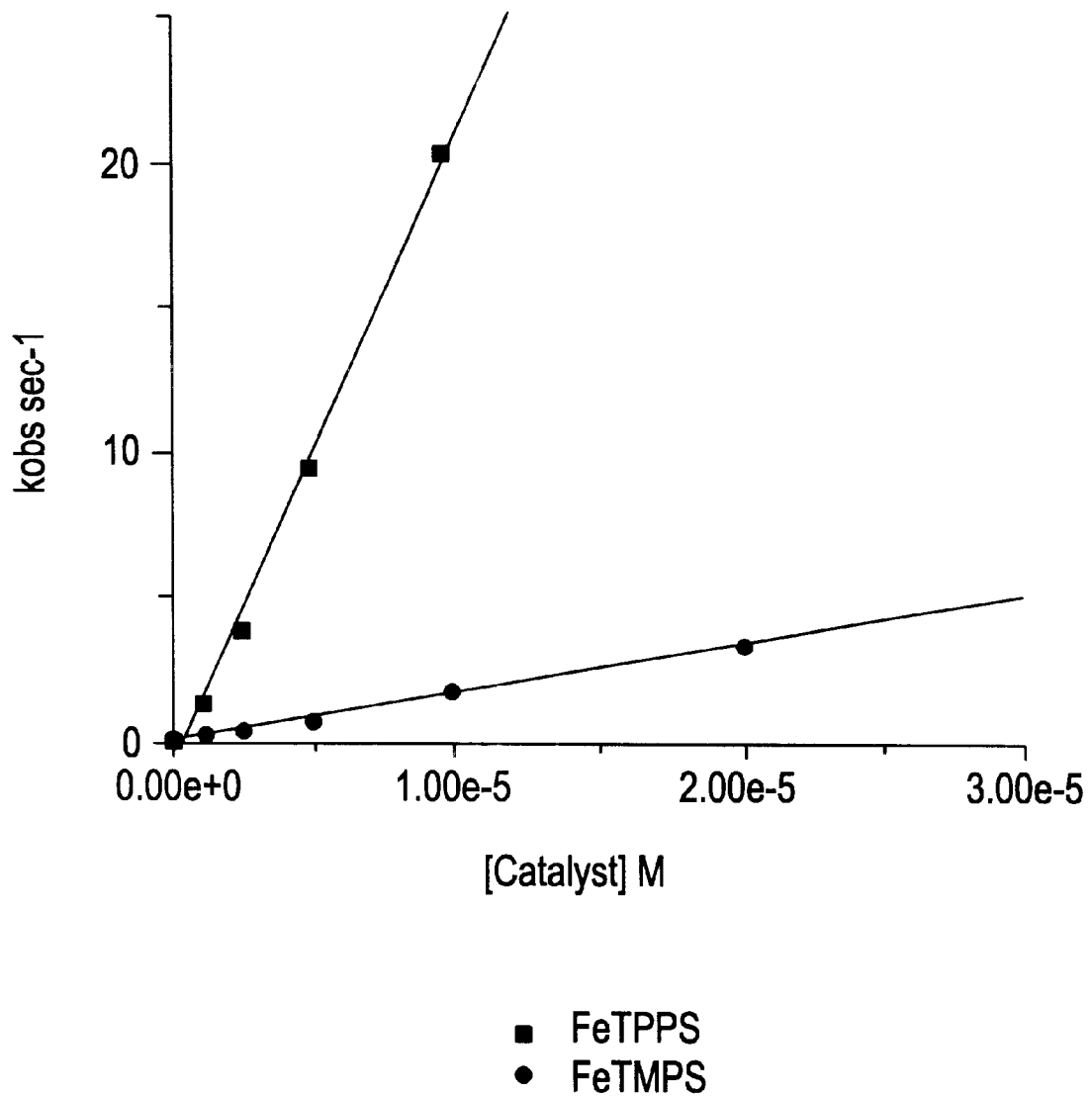

Chem. Res. Toxicol., vol. 5, No. 3, 1992, pp. 425–431, Moreno et al.

"Cold–Induced Brain Edema in Mice" in the Journal of Biological Chemistry, vol. 268, No. 21 Issue of Jul. 25, 1993, pp. 15394–15398.

23rd Annual Mtg. of the Society for Neuroscience, Washington, D.C., Nov. 7–12, 1993 and abstracted in Society For Neuroscience Abstracts 19(1–3), 1993 and Biosis 94:4951.

Palmer et al, Nature, 327, 1987, pp. 524–526, "Nitric Oxide Release Accounts for the Biological Activity of Endothelium–Derived Relaxing Factor".

Fostermann et al, Biochem. Phar. 42, 1991, pp. 1849–1857, "Isoforms of Nitric Oxide Synthase".

Hardy et al, FASEB Mtg. Apr. 5–9, 1992, Anaheim, CA., "Superoxide Mediates Human Aortic Endothelial Cell Damage by Stimulated Granulocytes".

Abstract for U.S. Patent 5,283,255 from O.G. Feb. 2, 1994, Levy et al.

Derwent Abstract 93–397684/50 for JP05277377–A.

Abstract for U.S. Patent 5,283,146 from O.G. Feb. 1, 1994, Ohashi et al.

Abstract for U.S. Patent 5,296,162 from O.G. Mar. 22, 1994, Itoh et al.

Absts. of 1st Annual Mtg. of Oxygen Society, Nov. 12–14, 1993, 4:22 Charleston, SC, "Nitric Oxide Requires Superoxide to Exert Bactericidal Activity", Brunelli et al.

Absts. of 1st Annual Mtg. of Oxygen Society, Nov. 12–14, 1993, 4:30 Charleston, SC, "Peroxynitrite Injury to Surfactant Protein A(SP–A)", Haddad et al.

Absts. of 1st Annual Mtg. of Oxygen Society, Nov. 12–14, 1993, 4:6 Charleston, SC, "The Nitration and Hydroxylation of Phenol and Salicylic Acid by Peroxynitrite", Koppenol et al.

METHODS OF USE FOR PEROXYNITRITE DECOMPOSITION CATALYSTS, PHARMACEUTICAL COMPOSITIONS THEREFOR

This is a FILE-WRAPPER CONTINUATION of application Ser. No. 08/431,593, filed May 1, 1995 which is a CIP of 08/242,498 filed May 13, 1994 now abandoned.

TECHNICAL FIELD

The present invention is for methods of use for the decomposition of peroxynitrite by metal complexes, novel pharmaceutical compositions, and methods of use therefor.

Particularly, the present invention now provides a method for treating selected diseases comprising the decomposition of peroxynitrite with the use of a compound which is a metal complex. This decomposition preferably produces benign agents preventing formation of deleterious decomposition products such as oxygen radicals and which also further prevents inactivation of superoxide dismutase (SOD) by the presence of peroxynitrite. Therefore, the method of use for selected metal complexes of the present invention, as well as novel pharmaceutical compositions for such use is for the treatment of diseases advantageously affected by treatment comprising decomposition of peroxynitrite at a rate accelerated over a natural background rate of decay which comprises administration of an rate-accelerating effective amount of the metal complex in unit dosage form.

In other words, the methods of treatment and novel compositions of this invention provide a twofold benefit in the treatment of diseases (1) accelerated rate of catalytic decomposition of peroxynitrite and (2) protection of SOD against inactivation by peroxynitrite.

Thus, the present invention provides for a method of treatment of human diseases advantageously affected by such decomposition by protection from the deleterious effects resulting from the presence of peroxynitrite in the human body not heretofore known. In addition, since protection against SOD inactivation is provided, such decomposition offers protection against diseases associated with the overproduction of superoxide.

These diseases include ischemic reperfusion injuries such as stroke, head trauma and myocardial ischemia, sepsis, chronic or acute inflammation (such as arthritis and inflammatory bowel disease and the like), adult respiratory distress syndrome, cancer, bronchopulmonary dysplasia, side effects from drug treatment of cancer, cardiovascular diseases, diabetes (not included for treatment by vanadium porphyrin complexes), multiple sclerosis, parkinson's disease, familial amyotrophic lateral sclerosis, and colitis and specific neuronal disorders, preferably ischemic reperfusion, inflammation, sepsis, multiple sclersis, parkinson's disease and stroke.

BACKGROUND ART

Nitric oxide (NO) is known for its dual physiological role as helpful messenger and harmful intermediate. Nitric oxide is shown to be generated in numerous cell types including macrophages, neutrophils, hepatocytes and endothelial cells. See Hibbs et al, *Science*, 1987,235,473–476; Rimele et al, *J. Pharmacol. Exp. Ther.*, 1988, 245, 102–111; Curran et al, *J. Exp. Med.*, 1989, 170, 1769–1774; and Plamer et al, *Nature*, 1987, 327, 524–526; respectively. The chemical reaction responsible for the production of NO is catalyzed by a class of enzymes referred to as nitric oxide synthases (NOS) which convert L-arginine to citrulline and NO. Forstermann et al, *Biochemical Pharmacology*, 1991,42, 1849–1857. While the role of NO as a signaling molecule in the stimulation of guanylate cyclase is well established, (Monocada et al, *Pharmacological Reviews*, 1991, 43, 109–142), the origins of its cytotoxicity remained unclear.

Recently a body of compelling evidence surfaced which teaches that NO by itself may not be responsible for cell damage (See Absts. of 1st Annual Mtg. of Oxygen Society, Nov. 12-4, 1993, Charleston, S.C., "Nitric Oxide Requires Superoxide to Exert Bactericidal Activity" by L. Brunnelli and J. S. Beckman). Instead a more reactive species, peroxynitrite, produced by the reaction of superoxide and NO, is found to play a role in the cytotoxicity observed with the over-production of NO. Peroxynitrite is known to decompose via a process which is first order in protons. The rate of proton catalyzed decomposition of peroxynitrite (hereinafter "the natural background rate of decay") is understood from its study over a variety of pH ranges (see; Keith et al. *J Chem Soc* (A), p.90, 1969). When the pH is 7.4 and the temperature is maintained at 37° C., the observed rate for the decomposition of peroxynitrite is $3.6 \times 10^{-1}$ sec-i (see Beckman et al. *Proc. Natl. Acad. Sci. USA* Vol 87, pp. 1620–1624, 1990). Beckman shows that peroxynitrite decomposition generates a strong oxidant with reactivity similar to hydroxyl radical, as assessed by the oxidation of deoxyribose or dimethyl sulfoxide with the further suggestion that superoxide dismutase protects vascular tissue stimulated to produce superoxide and NO under pathological conditions by preventing the formation of peroxynitrite. See Beckman et al, "Apparent Hydroxyl Radical Production by Peroxynitrite: Implications for Endothelial Injury from Nitric Oxide and Superoxide" in *Proc. Natl. Acad. Sci. USA*, Vol. 87, pp 1629–1624, February 1990.

Further, it is well established that peroxynitrite decomposes to give the hydroxyl radical and nitrogen dioxide, a potent nitrating agent. Both of these species are potent oxidants shown to react with lipid membrane and sulfhydryl moieties (See Radi et al "Peroxynitrite Oxidation of Sulfhydryls" in *The Journal of Biological Chemistry*, Vol. 266, No. 7 March 5, pp 4244–4250, 1991).

Hardy et al suggest the interaction of $O_{2-}$ with nitric oxide forms peroxynitrite or the protonation of $O_{2-}$ to form perhydroxyl radical is involved in the neutrophil-meditated killing of HAE cells (FASEB Meeting on Apr. 5–9, 1992 in Anaheim, Calif.) and further Hardy et al suggest a role for peroxynitrite in oxidative damage of human endothelial cells (Abstract in the "Experimental Biology" section of FASEB on Mar. 28–Apr. 1, 1993 in New Orleans, La.).

In other words, harmful products from peroxynitrite decomposition is specifically taught by many references.

In addition, it has been shown that the reaction of peroxynitrite with Mn and Fe SOD results in inactivation of the enzyme (See also Radi et al, *Arch. Biochem. Biophys.*, 1991, 288, 481–487). It is now known that peroxynitrite will also inactivate CuZn SOD.

Thus, the effects of the decomposition of peroxynitrite; whether by the generation of damaging decomposition products or inactivation of SOD, in a wide variety of diseases are well documented.

For example, a study assessing the deleterious effects of peroxynitrite on the rat colon is reported by Rachmilewitz et al in "Peroxynitrite-induced Rat Colitis: A New Model of Colonic Inflammation" from Gastroenterology 105 (6) 1993.

Beckman et al in PCT/US91/07894 (corresponding to U.S. Pat. No. 5,277,908) teach, specifically that peroxynitrite is formed by the reaction of superoxide ($O_{2-}$) and nitric oxide in tissues subjected to ischemic, inflammatory or septic conditions. Beckman et al link SOD deficiencies and peroxynitrite to amyotrophic lateral sclerosis (ALS) in *Nature*, Vol 364, 12 August 1993 and Hogg et al and Beckman et al., respectively, present a relationship between peroxynitrite and atherosclerosis in *Biochemical Society Transactions*, Vol. 21, received Dec. 22, 1992 and in "Extensive Nitration of Protein Tyrosines in Human Atherosclerosis Detected by Immunohistochemistry", *Biol Chem. Hoppe-Sevler*, Vol. 375, pp 81–88, February 1994. Further, the involvement of peroxynitrite in various disease states is found for lung diseases attributed to cigarette smoke, atherosclerosis, amyotrophic lateral sclerosis, cold-induced brain edema in *Chem. Res. Toxicol.*, Vol. 5, No. 3, 1992 pp 425–431. See also "Cold-induced Brain Edema in Mice" in *The Journal of Biological Chemistry*, Vol.268, No. 21 Issue of July 25, pp 15394-15398, 1993.

More recently a spinal neuron toxicity assay has been developed by Scherch et al to screen for drugs which block peroxynitrite toxicity. (23rd Annual Meeting of the Society for Neuroscience, Washington, D. D., Nov. 7–12, 1993 and abstracted in *Society for Neuroscience Abstracts* 19 (1–3) 1993 and *Biosis* 94:4951.

Further, by preventing inactivation of SOD by reducing the presence of peroxynitrite the present invention also provides enhancement of known physiological benefits of superoxide dismutase in the treatment of diseases based on such benefits. In this regard SOD and its mimics have been shown to be useful in the treatment of diseases for the inhibition of an overproduction of superoxide and nitric oxide. Thus, the present invention relates to the known treatment for diseases by SOD and SOD mimics.

The Beckman et al PCT application also teaches that SODs catalyze the dismutation of the oxygen radical superoxide and provides references which show SOD and variants thereof have been commonly utilized to prevent or reduce oxidation injury in the treatment of stroke and head trauma, myocardial ischemia, abdominal vascular occlusion, cystitis, and a variety of inflammatory conditions. Beckman et al PCT application also recognizes the presence of peroxynitrite in these same disease conditions associated with $O_{2-}$ without indicating the further improvements of the present invention.

Further teachings to the diseases known to be associated with treatment by SOD or its mimics are found in EP Publication No. 0524161 (EP Appl. No. 92870097) which is incorporated by reference therefor.

Porphyrin complexes are disclosed in U.S. Pat. No. 5,284,674 as valuable diagnostic and therapeutic agents, non-peptide phaeophorbide analogs are disclosed in Japanese Patent Publication Hei 5-331063 as endocerine receptor antagonists, carotenoporphyrins are disclosed in U.S. Pat. No. 5,286,474 to be valuable for locating and visualizing mammalian tumor tissue and similar nitrogen containing macrocycles without a complexed metal are disclosed as cytotoxic agents in U.S. Pat. No. 5,283,255. No metal complexes and their usefulness are shown as now found in the present invention.

Metal complexes are, however, shown to be useful compounds in Derwent Abstract as intermediates in JP05277377-A and MRI agents in U.S. Pat. No. 5,284,944; cyan pigments in U.S. Pat. No. 5,286,592; photoconductive phthalocyanine compositions in U.S. Pat. No. 5,283,146; a recording layer in an optical recording medium in U.S. Pat. No. 5,284,943 and near infrared absorbers and display/recording materials in an abstract for U.S. Pat. No. 5,296,1632.

Iron hemoprotein is disclosed to be an effective agent to bind or oxidize nitric oxide which has a deleterious physiological effect when induced by a cytokine or by endotoxin for the treatment of diseases such as septic shock in PCT application No. PCT/US93/01288 (Publication No. WO 93/16721).

Other complexes and their utilities are disclosed. For example, "Ruthenium Phthalocyanines" are disclosed as water soluble agents for photodynamic cancer Therapy in *Platinum Metals Rev.*, 1995, 39, (1), 14–18; selected metallo-organic complexes are disclosed as treatment of inflammation in U.S. Pat. No. 4,866,054; Porphyrin and phthalocyanine antiviral compositions are disclosed as inhibitors of infection or replication of HIV in U.S. Pat. No. 5,109,016; Manganese meso-tetra(4-sulfonatophenyl) porphine are synthesized and used as tumor-selective MRI contrast agents; an abstract for JP 03273082 teaches peroxide-degrading metal porphyrins for use as antioxidants in the manufacture of foods or other products; U.S. Pat. No. 4,758,429 teaches iron tetraphenyl porphyrin sulfonate acetate for activating magnetic or electrical dipoles in the joint with an alternating electromagnetic field to treat arthritis and non-infectious joint diseases; an abstract of EP 392666 shows a non-toxic labile metal atom or complex such as 1,5,9,13-tetrazacyclohexadecane for use in the treatment of a virus such as HIV. CA 119:203240 discloses selected metalloporphyrins as hypoplycemics are found in French Patent No. 91-6174. Numerous additional references indicate analogous additional uses for metal complexes.

Finally, nitrogen containing selected macrocycles are shown in JPO5331063 as endothelin receptor antagonists for treating and preventing hypertension, acute renal failure, cardiomyopathy and myocardial infarction.

SUMMARY OF THE INVENTION

The present invention is a method of treating a disease which is advantageously affected by decomposition of peroxynitrite which is accelerated over, ie above or more than, a natural background rate of decay in humans suffering from the disease comprising administering a compound or compound which is a metal complex whereby the peroxynitrite is decomposed. Preferably peroxynitrite is decomposed to a benign species. The compound is a ligand structure providing a complexed metal, such as one of the transition metals, such as Mn, Fe, Ni and V. Preferred ligands are macrocyclic ligands, such as porphyrins, aza macrocycles and the like.

The present invention is a novel method of treating a disease in mammals, including humans, advantageously affected by the absence of peroxynitrite comprising administration of an accelerated-decomposition effective amount of a compound of the formula Structure I

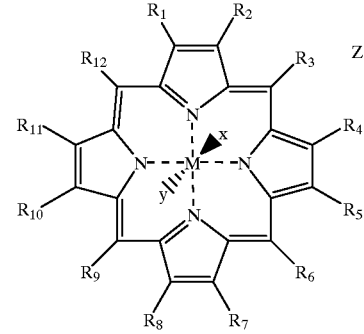

wherein $R_3$, $R_6$, $R_9$ or $R_{12}$ are independently selected a group consisting of H, alkyl, alkenyl, $CH_2COOH$, phenyl, pyridinyl, and N-alkylpyridyl such that phenyl, pyridinyl and N-alkylpyridyl are

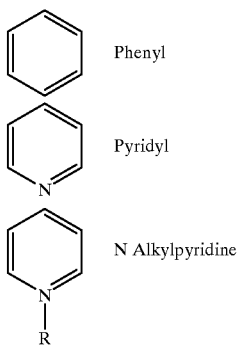

Phenyl

Pyridyl

N Alkylpyridine which are attached at a carbon atom, and
wherein phenyl is optionally substituted by halogen, alkyl, aryl, benzyl, COOH, CONH$_2$, SO$_3$H, NO$_2$, NH$_2$, N(R)$_{3+}$, wherein R is hydrogen, alkyl, or alkylaryl;
pyridinyl is optionally substituted by halogen, alkyl, aryl, benzyl, COOH CONH$_2$, SO$_3$H, NO$_2$, NH$_2$, N(R)$_{3+}$ or NHCOR' wherein R is as defined above and R' is alkyl; and
N-alkylpyridine ring is optionally substituted by halogen, alkyl, aryl, benzyl, COOH, CONH$_2$, SO$_3$H, NO$_2$, NH$_2$, N(R)$_{3+}$ or NHCOR' wherein R and R' are as defined above;

$R_1$, $R_2$, $R_4$, $R_5$, $R_7$, $R_8$, $R_{10}$, or $R_{11}$ are independently selected a group consisting of H, alkyl, alkenyl, carboxyalkyl, Cl, Br, F, NO$_2$, hydroxyalkyl, and SO$_3$H or $R_1$ and $R_2$ can be taken together to form a ring of from 5 to 8 carbons preferably 6;

X and Y are suitable ligands or charge-neutralizing anions which are derived from any monodentate or polydentate coordinating ligand or ligand system or the corresponding anion thereof (for example benzoic acid or benzoate anion, phenol or phenoxide anion, alcohol or alkoxide anion) and are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl, amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid (such as acetic acid, trifluoroacetic acid, oxalic acid), aryl carboxylic acid (such as benzoic acid, phthalic acid), urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkyl aryl thiocarbamate, alkyl dithiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroanitmonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or systems; with the proviso that when the X and Y containing complex has a net positive charge then Z is present and is a counter ion which is independently X or Y, or when the X and Y containing complex has net negative charge then Z is present and is a counter ion selected from a group consisting of alkaline and alkaline earth cations, organic cations such as alkyl or alkylaryl ammonium cations; and M is selected from the group consisting of Mn, Fe, Ni and V;

Structure II

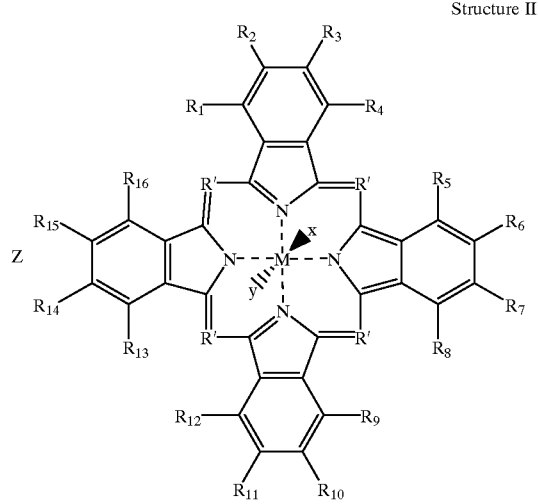

wherein
R' is CH or N;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are independently selected from a group consisting of H, SO$_3$H, COOH, NO$_2$, NH$_2$, and N-alkylamino;
X, Y, Z and M are selected as defined above;

Structure III

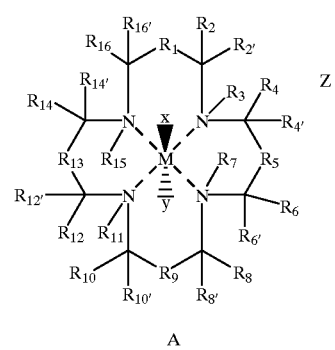

A wherein
$R_1$, $R_5$, $R_9$, and $R_{13}$ are independently a direct bond or CH$_2$;

$R_2$, $R_2'$, $R_4$, $R_4'$, $R_6$, $R_6'$, $R_8$, $R_8'$, $R_{10}$, $R_{10}'$, $R_{12}$, $R_{12}'$, $R_{14}$, $R_{14}'$, $R_{16}$, $R_{16}'$ are independently H, or alkyl;
$R_3$, $R_7$, $R_1$, $R_{15}$ are independently H or alkyl;
X, Y, Z and M are as defined above;

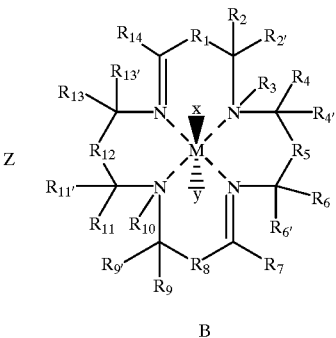

B wherein
$R_1$, $R_5$, $R_8$, and $R_{12}$ are independently a direct bond or $CH_2$;
$R_2$, $R_2'$, $R_4$, $R_4'$, $R_6$, $R_6'$, $R_7$, $R_9$, $R_9'$, $R_{11}$, $R_{11}'$, $R_{13}$, $R_{13}'$, $R_{14}$ are independently H or alkyl;
$R_3$ and $R_{10}$ are independently H or alkyl;
X, Y, Z and M are as defined above;

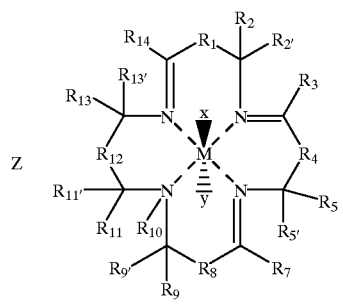

C wherein
$R_1$, $R_4$, $R_8$, $R_{12}$ are independently a direct bond or $CH_2$;
$R_2$, $R_2'$, $R_3$, $R_5$, $R_5'$, $R_7$, $R_9$, $R_9'$, $R_{11}$, $R_{11}'$, $R_{13}$, $R_{13}'$, $R_{14}$ are independently H or alkyl;
$R_{10}$ is H or alkyl;
X, Y, Z and M are as defined above;

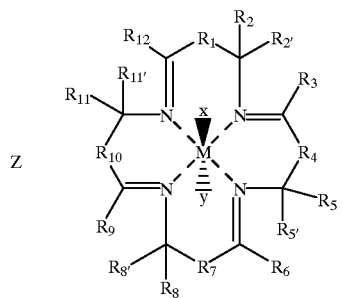

D wherein
$R_1$, $R_4$, $R_7$ and $R_{10}$ are independently a direct bond or $CH_2$;

$R_2$, $R_2'$, $R_3$, $R_5$, $R_5'$, $R_6$, $R_8$, $R_8'$, $R_9$, $R_{11}$, $R_{11}'$ and $R_{12}$ are independently H or alkyl;
X, Y, Z and M are as defined above;

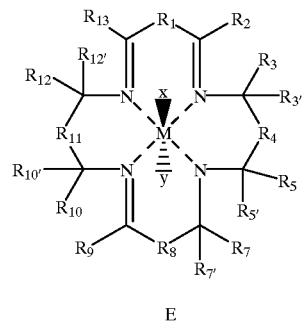

E wherein
$R_1$, $R_4$, $R_8$ and $R_{11}$ are independently a direct bond or CH2;
$R_2$, $R_3$, $R_3'$, $R_5$, $R_5'$, $R_7$, $R_7'$, $R_9$, $R_{10}$, $R_{10}'$, $R_{12}$, $R_{12}'$ and $R_{13}$ are dependently H or alkyl;
$R_6$ is hydrogen and alkyl;
X, Y, Z and M are as defined above;

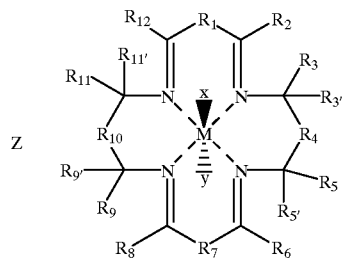

F wherein
$R_1$, $R_4$, $R_7$ and $R_{10}$ are independently H or alkyl;
$R_2$, $R_3$, $R_3'$, $R_5$, $R_5'$, $R_6$, $R_8$, $R_9$, $R_9'$, $R_{11}$, $R_{11}'$ and $R_{12}$ are independently H or alkyl;
X, Y, Z and M are as defined above;

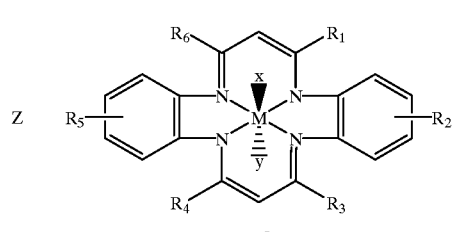

G wherein
$R_1$, $R_3$, $R_4$ and $R_6$ are independently H or alkyl;
$R_2$ and $R_5$ are independently selected from the group consisting of H, alkyl, $SO_3H$, $NO_2$, $NH_2$, halogen, COOH, and $N(R)_{3+}$ wherein R is as defined above;

X, Y, Z and M are as defined above;

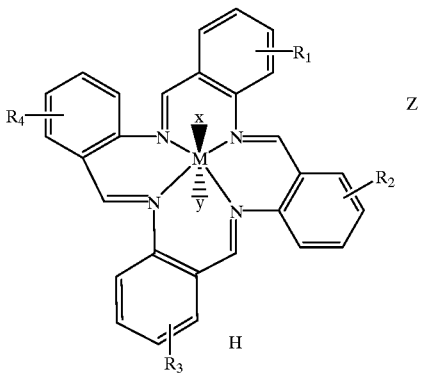

wherein
R$_1$, R$_2$, R$_3$, R$_4$ are independently selected from the group consisting of H, alkyl, SO$_3$H, NO$_2$, NH$_2$, halogen, COOH and N(R)$_{3+}$ wherein R is as defined above;
X, Y, Z and M are as defined above;

Structure IV

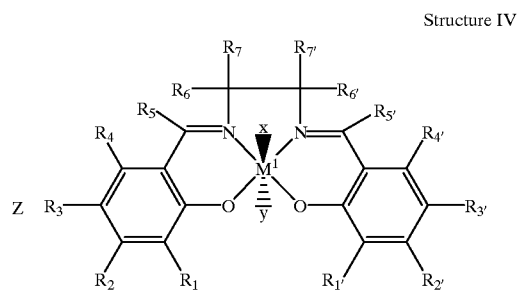

wherein
R1, R1', R2, R2', R3, R3', R4, R4', R5, R5', R6, R6', R7 and R7' are independently selected from a group consisting of H, alkyl, alkoxy, NO$_2$, aryl, halogen, NH$_2$, SO$_3$H, and R$_6$, R$_6$', R$_7$ and R$_7$' may each be taken together with one other of R$_6$, R$_6$', R$_7$ and R$_7$' to form a cyclic group, preferably a 6 carbon cycloalkyl group;
M$^1$ is Fe, Ni or V;
X, Y and Z are as defined above together with a pharmaceutically acceptable carrier, preferably in unit dosage form.

The present invention is also a pharmaceutical composition for the treatment of a disease in humans advantageously affected by accelerated decomposition over the natural background rate of decay of peroxynitrite comprising an amount effective for the accelerated decomposition of peroxynitrite in humans of a compound of the formula I, II, IIIA, IIIB, IIIC, IIID, IIIE, IIIF, IIIG, IIIH as defined above with a pharmaceutically acceptable carrier in unit dosage form, preferably oral unit dosage form.

BRIF DESCRIPTION OF THE DRAWINGS

FIG. 1: Plot of k$_{obs}$ vs catalysts concentration for Fe(III) TMPS and Fe(III)TPPS illustrating catalytic nature of decomposition of peroxynitrite by metal complexes.

Figure 2:
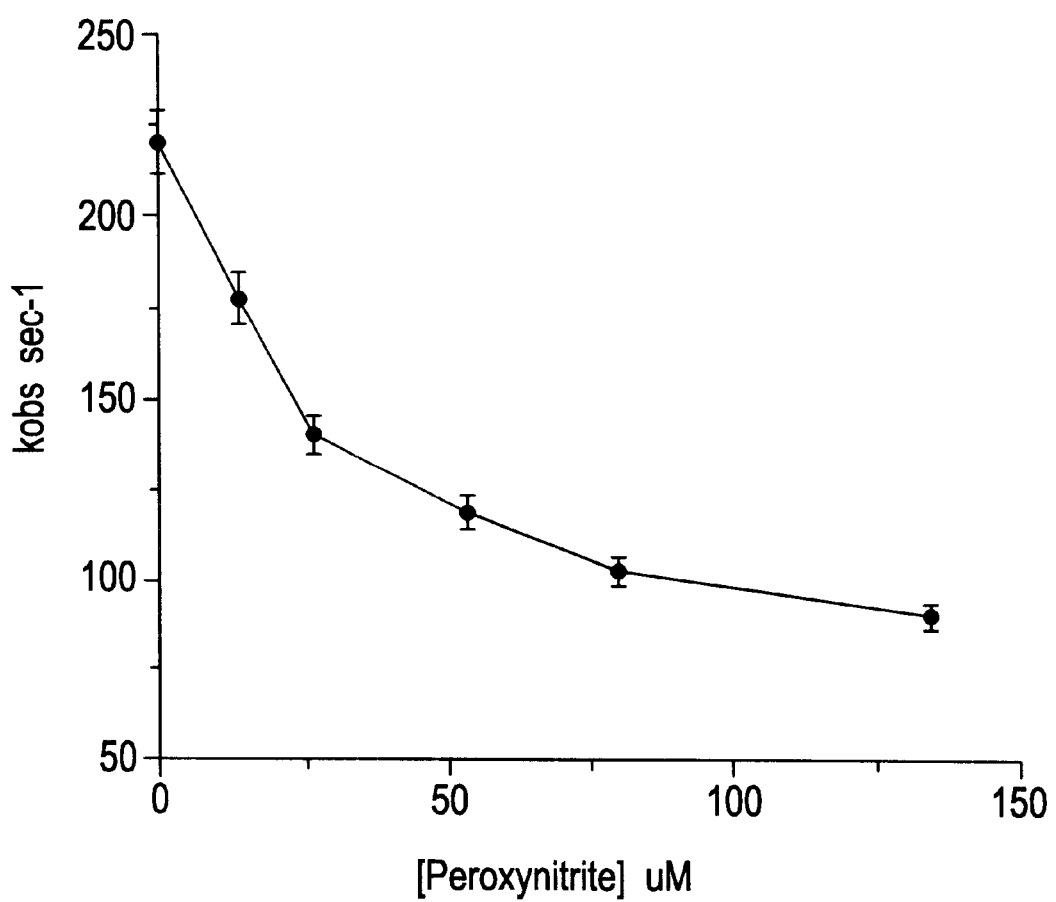

FIG. 2: Plot illustrating the inactivation of CuZnSOD by peroxynitrite.

Figure 3:
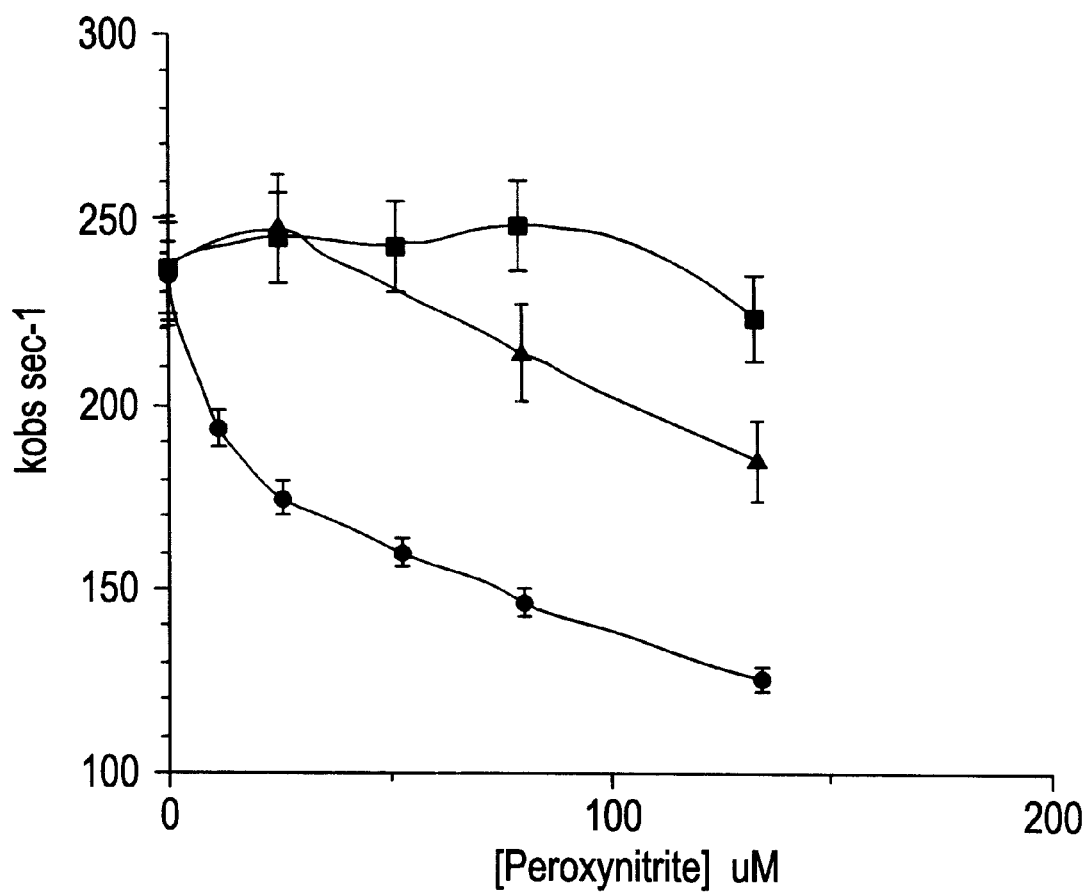

FIG. 3: Plot illustrating the concentration dependant protection of CuZnSOD against inactivation by peroxynitrite using peroxynitrite decomposition catalysts Fe(III)TMPyP.

Figure 4:
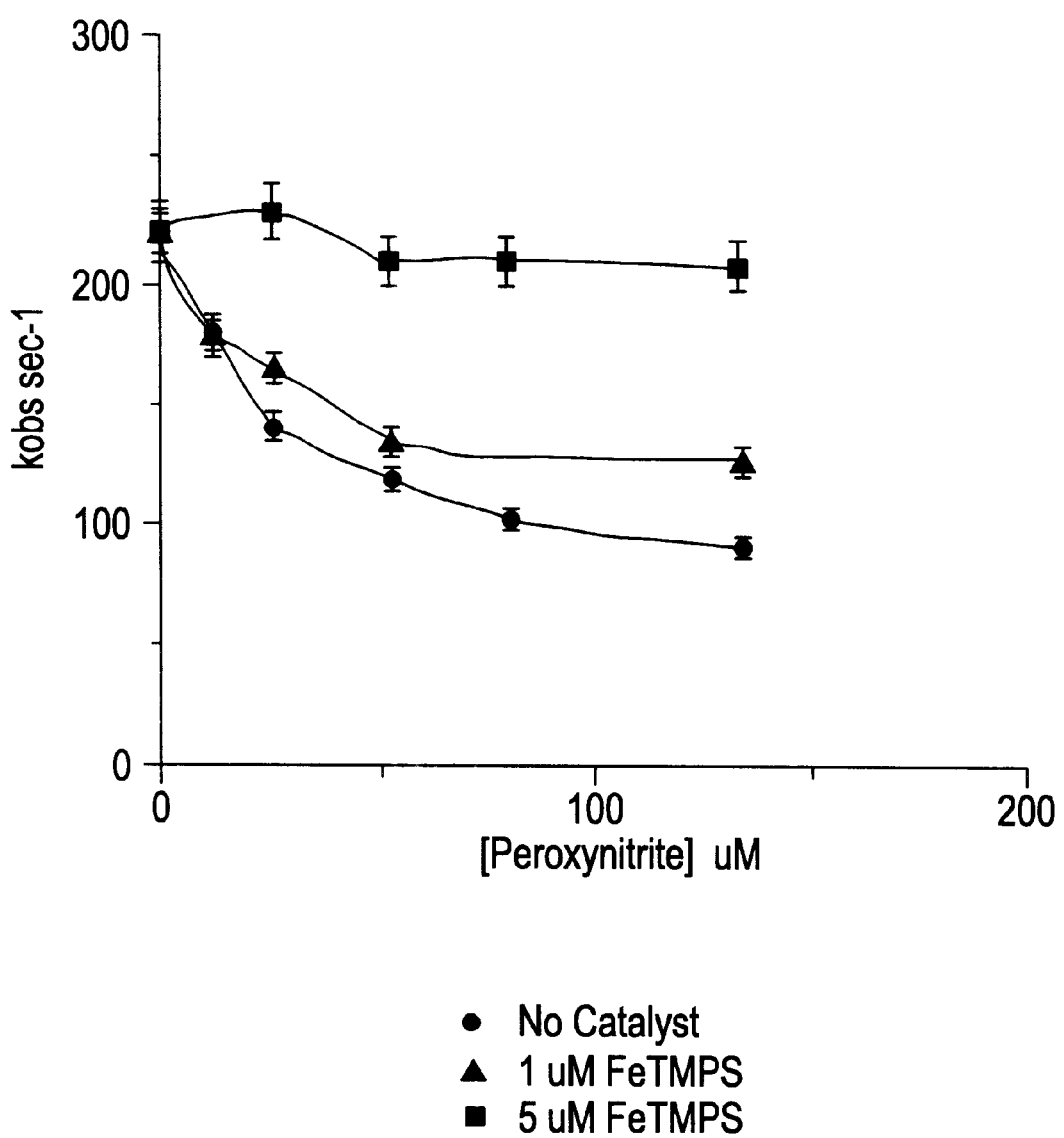

FIG. 4: Plot illustrating the concentration dependant protection of CuZnSOD against inactivation by peroxynitrite using peroxynitrite decomposition catalyst Fe(III)TMPS.

Figure 5:
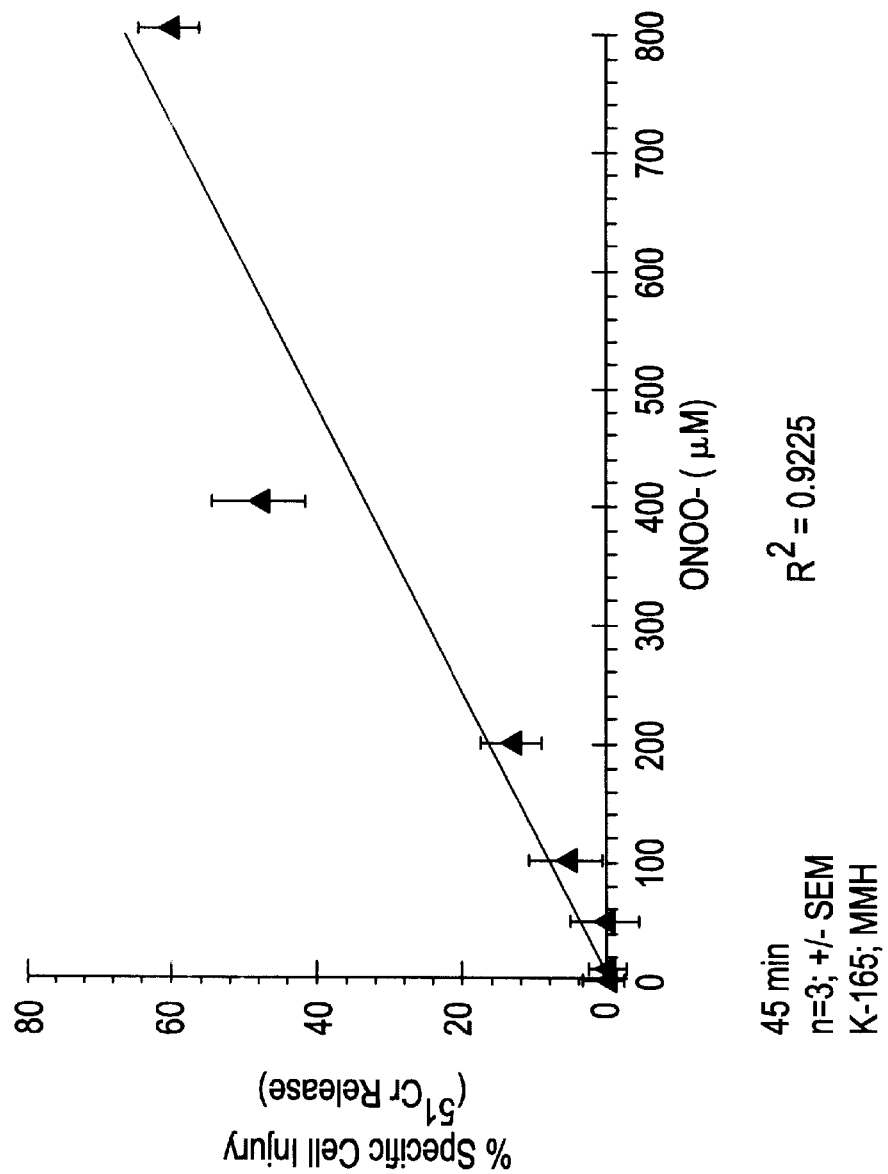

FIG. 5: Peroxynitrite-mediated human microvascular endothelial cell injury. Authentic peroxynitrite was overlaid directly onto to $^{51}$Cr-labeled HMDE cells grown in 96-well cell culture plates. After 45 min the amount of specific cell injury was determined and correlated to peroxynitrite concentration by least squares regression line. Values represent the average of three replicates +/−SEM.

Figure 6:
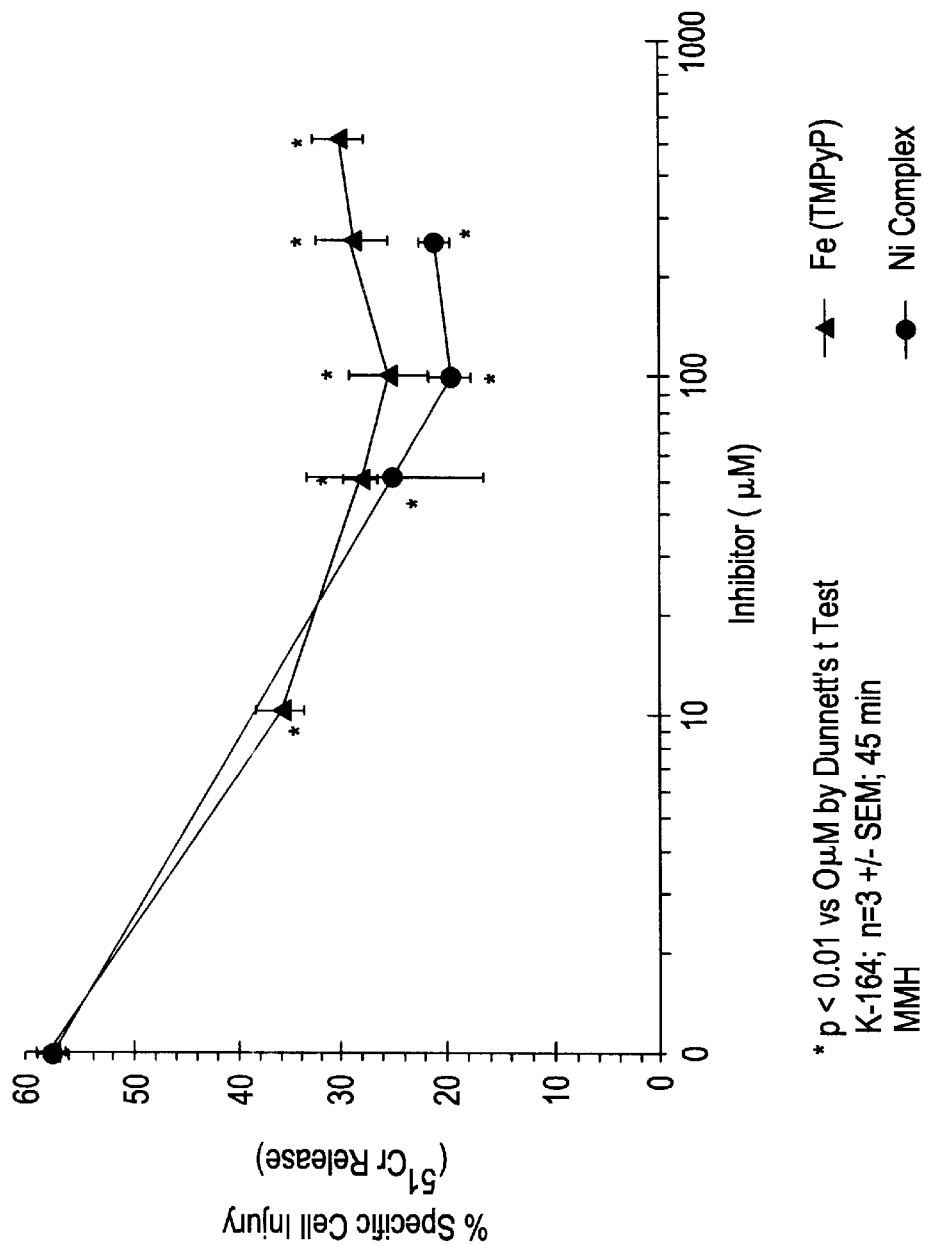

FIG. 6: Peroxynitrite catalysts, Fe(TMPyP) (triangle) and Ni(II)dienoN$_4$)PF$_6$(circle) were added to HDME cells in the cell injury assay immediately before the addition of authentic peroxynitrite. After 45 min, the amount of specific cell injury was assessed by the amount of radiolabel released into the medium. Values represent the average of three replicas +/−SEM. *p<0.01 vs. 0 uM control by Dunnett's t Test.

Figure 7:
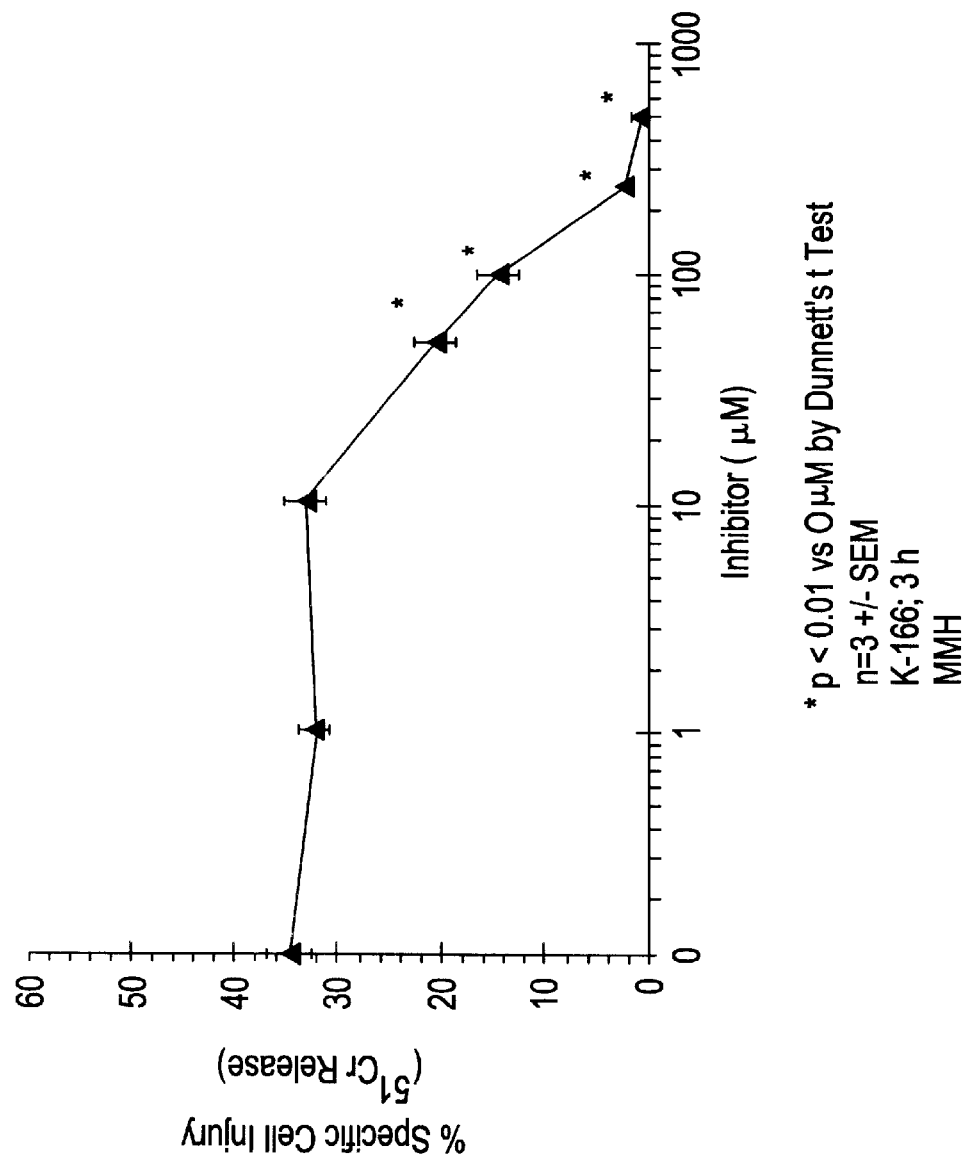

FIG. 7: Inhibition of neutrophil-mediated injury to human aortic endothelial cells by Fe(TMPyP). Peroxynitrite catalyst, Fe(TMPyP), was added to neutrophils in the cell injury assay immediately before activation by TNF/C5a. After 2 h, the amount of specific cell injury was assessed by the amount of radiolabel released into the medium. Values represent the average of three replicas +/−SEM. *p<0.01 vs. 0 uM control by Dunnett's t Test.

Figure 8:
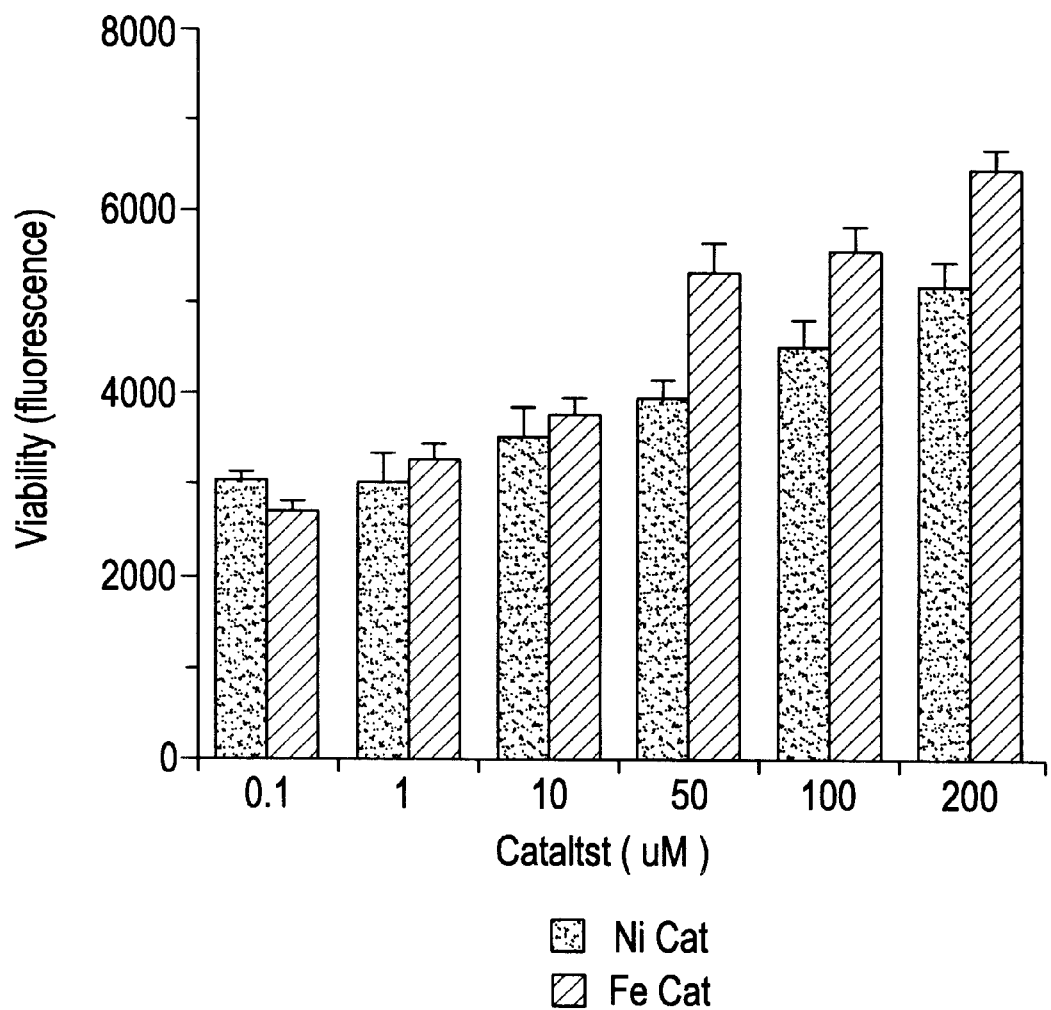

FIG. 8: Comparison of Ni and Fe Catalyst Protection of RAW Cells from PN(peroxynitrite)-mediated Injury. RAW 264.7 cells were plated at approximately 2×10$^5$ per well of a 96-well plate. PN(360 micromolar) was added to every well of cells in the presence of increasing concentrations of Ni catalyst or FeTMPyP resulting in total protection from PN-mediated injury as determined by the ability of cells to metabolize Alamar Blue to a fluorescent product. Each condition represents the mean of 4 wells ±sem.

Figure 9:
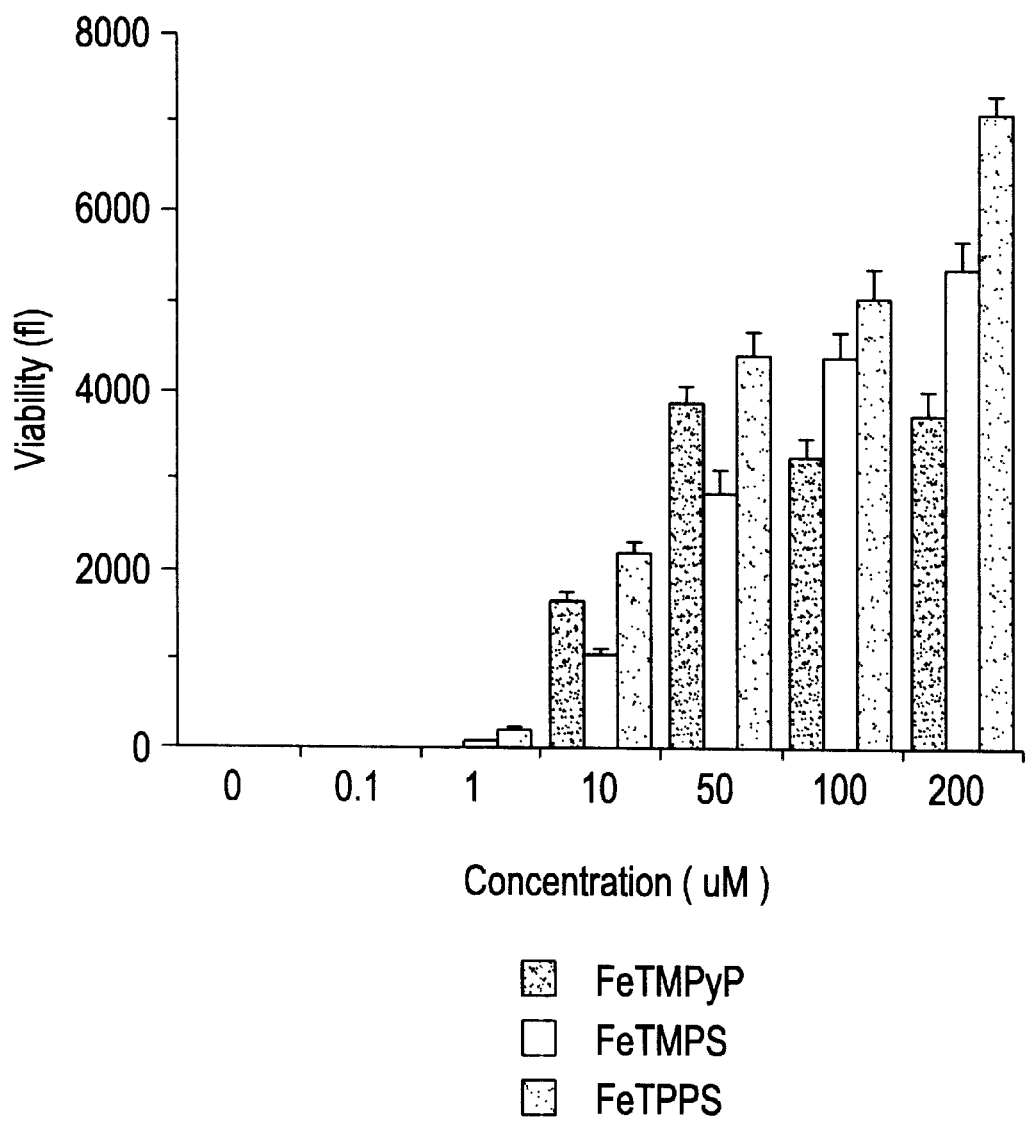

FIG. 9: Protection from PN-mediated RAW Cell Injury by Fe Catalysts. Cells were treated with 500 micromolar PN in the presence or the absence of the following catalysts: FeTMPyP, FeTMPS, FeTPPS. Cell viability was monitored as described in the text and figure legends 1, 2 and 3. Values represent the mean of 4 determinations ±sem.

Figure 10:
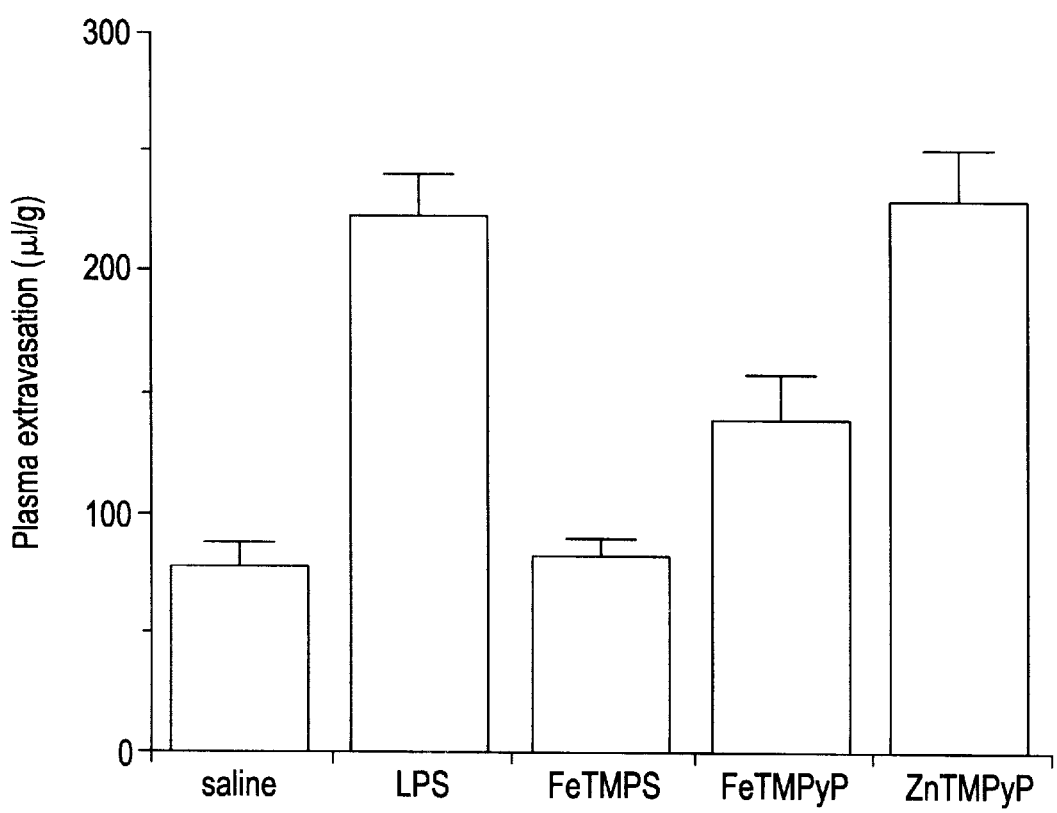

FIG. 10. Effects of FeTMPS, FeTMPyP or ZnTMPyP (30 mg/kg, i.v bolus) administered 3 h after challenge with E. coli lipopolysaccharide (LPS, 3 mg/kg, i.v bolus) on the increase in leakage of radio-labelled albumin (plasma extravasation, μl/g tissue) observed 1 h later (e.g 4 h after LPS challenge) in the rat jejunum. Results are shown as mean±s.e.m of 4–8 rats.

DETAILED DESCRIPTION OF THE INVENTION

As utilized herein, the term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms. Examples of such radicals include, but are not limited to methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl. The term "aryl", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl or cycloalkyl radical as defined herein in which one hydrogen atom is replaced by an aryl radical as defined herein, such as benzyl, 2-phenylethyl, and the like. The term "heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. The term "cycloalkyl", alone or in combination means a cycloalkyl radical containing from 3 to about 10, preferably from 3 to about 8, and most preferably from 3 to about 6 carbon atoms. Examples of such cycloalkyl radicals include, but are not limited to, cyclopropyl, cyclobutyl, cyclophetyl, cyclohexyl, cycloheptyl, cyclooctyl, and perhydronaphthyl. The term "cycloalkenyl", alone or in combination, means a cycloalkyl radical having one or more double bonds. Examples of cycloalkenyl radicals include, but are not limited to cyclopentenyl, cyclohexenyl, cyclooctenyl, cyclopentadienyl, cyclohexadienyl, and cyclooctadienyl.

The macrocyclic ligands useful in the present invention wherein the formula is Structure I can be prepared according to the general synthetic methods known in the art for preparation of certain ligands. See, for example,
1) Campestrini, S.; Meunier, B. Inorg. Chem. 31, 1999–2006, (1992).
2) Robert, A.; Loock, B.; Momenteau, M.; Meunier, B. Inorg. Chem. 30, 706–711, (1991).
3) Lindsey, J. S.; Wagner, R. W. J. Org. Chem. 54, 828–836, (1989).
4) Zipplies, M. F.; Lee, W. A.; Bruice, T. C. J. Am. Chem. Soc. 108, 4433–4445, (1986).

The macrocyclic ligands useful in the present invention wherein the formula is Structure II can be prepared according to the general synthetic methods known in the art for preparation of certain ligands. See, for example,
1) Some compounds are commercially available from Porphyrin Products, Inc. (Logan, Utah.)
2) Y. L. Meltze; Phthalocyanine Technology in Chemical Process Reviews No. 42.; Noyes Data Corp, Park Ridge, N.J. (1970).

The macrocyclic ligands useful in the present invention wherein the formula is Structure III can be prepared according to the general synthetic methods known in the art for preparation of certain ligands. See, for example,
1) Goedken, V. L.; Molin-Case, J.; Whang, Y-A; J.C.S.Chem.Comm. 337–338, (1973)
2) Martin, J. G.; Cummings, S. C.; Inorg.Chem. 12, 1477–1482, (1973).
3) Riley, D. P.; Stone, J. A.; Busch, D. H. J.Am.Chem.Soc. 98, 1752–1762, (1976).
4) Dabrowiak, J. C.; Merrell, P. H.; Stone, J. A.; Busch, D. H.; J.Am.Chem.Soc. 95, 6613–6622, (1973).
5) Riley, D. P.; Busch, D. H.; Inorg. Chem. 23, 3235–3241, (1984).
6) Watkins, D. D.; Riley, D. P.; Stone, J. A.; Busch, D. H.; Inorg. Chem. 15, 387–393, (1976).
7) Riley, D. P.; Stone, J. A.; Busch, D. H.; J.Am.Chem.Soc. 99, 767–777, (1977).

The macrocyclic ligands useful in the present invention wherein the formula is Structure IV can be prepared according to the general synthetic methods known in the art for preparation of certain ligands. See, for example,
1) Diehl, H.; Hoch, C. C.; Inorganic Synthesis Vol 3. p 196. McGraw-Hill, New York (1950).
2) Srinivasan, K; Michaud, P.; Kochi, J. K; J. Am. Chem. .Soc. 108, 2309–2320, (1986).
3) Samsel, E. G.; Srinivasan, K.; Kochi, J. K J. Am. Chem. Soc. 107, 7606–7617, (1985).

The compounds of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

To screen metal complexes for peroxynitrite decomposition catalytic activity of the present invention, peroxynitrite is prepared and isolated as its sodium salt by the reaction of acidic hydrogen peroxide with sodium nitrite followed by rapid quenching with NaOH as set out by Halfpenny and Robinson, in J. Chem. So., 1952, 928–938. Peroxynitrite has an absorbance maximum at 302 nm with an extinction coefficient of 1670 $M^{-1}cm^{-1}$. Therefore, it is possible to directly observe the decomposition of peroxynitrite by stop-flow spectrophotometric analysis by monitoring the decomposition of the absorbance at 302 nm. That is, such observation of the decomposition of peroxynitrite at a rate accelerated over the natural decomposition rate with the addition of the metal complex identifies a compound of the present invention.

In addition, it is now found that peroxynitrite inactivates CuZnSOD enzyme in a concentration dependant manner. Since it is known peroxynitrite also inactivates MnSOD (See "Peroxynitrite-Mediated Tyrosine Nitration Catalyzed by Superoxide Dismutase" by Ischiropoulos et al in Archives of Biochemistry and Biophysics, Vol. 298, No. 2, November 1, pp. 431–437, 1992), the present invention provides a compound which protects CuZnSOD from inactivation by peroxynitrite.

In this manner the compound of the present invention is shown to be useful in treating a disease in a human advantageously affected by the presence of the SOD enzyme.

That is, the treatment of the present invention is for a disease state either caused by the presence of a peroxynitrite of caused by the lack of the protective presence of the SOD enzyme such as in a myocardial infarct, stroke or an autoimmune disease. These latter diseases are also shown to be associated with the presence of peroxynitrite.

These metal complexes are found to be within the present invention by determination of their decomposition effect on peroxynitrite as set out herein.

Contemplated equivalents of the general formulas set forth above for the compounds and derivatives as well as the intermediates are compounds otherwise corresponding thereto and having the same general properties such as tautomers of the compounds and such as wherein one or more of the various R groups are simple variations of the substituents as defined therein, e.g., wherein substituents which are a higher alkyl group than that indicated, or where the tosyl groups are other nitrogen or oxygen protecting groups or wherein the O-tosyl is a halide. Anions having a charge other than 1, e.g., carbonate, phosphate, and hydrogen phosphate, can be used instead of anions having a charge of 1, so long as they do not adversely affect the overall activity of the complex. However, using anions having a charge other than 1 will result in a slight modification of the general formula for the complex set forth above. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions shown by the references described above are generally disclosed in terms of variations appropriate for their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

All reagents were used as received unless otherwise indicated. 5,10,15,20-tetrakis(N-Methyl-4-pyridyl) porphyrin tetratosylate and Acetato-5,10,15,20-tetrakis(4-sulfonatophenyl)porphyrin iron(III) were purchased from Porphyrin Products Inc. (Logan, Utah). Iron(III)citrate and iron(III)EDTA complexes were purchased from Aldrich Chemical Co. (Milwaukee, Wis.). All nuclear magnetic resonance (NMR) spectra were obtained on Varian VXR-300 or Varian VXR-400 spectrometers. Qualitative and quantitative mass spectra were run on a Finnigan MAT90, a Finnigan 4500 and a VG40-250T spectrometers.

Example 1
Synthesis of Acetato (5,10,15,20-tetrakis(N-methyl-4-pyridyl)porphinato) iron (III) tetra-tosylate, Fe(III)TMPyP.

5,10,15,20-Tetra-(N-methyl-pyridyl)porphine tetratosylate, ($H_2$TMPyP) (0.30 g, 0.231 mmole) was charged to a 100 mL round bottom flask equipped with a magnetic stir bar and was dissolved in a minimal amount of MeOH. Anhydrous Fe(OAc)$_2$ (0.120 g, 0.692 mmole) was added followed immediately by 25 mL of glacial acetic acid and 100 uL of triethylamine. The reaction mixture was heated to reflux. The reaction was monitored by visible spectroscopy and was determined to be complete with the appearance of a strong band at 426 nm indicative of the metallated porphyrin. The MeOH was removed by evaporation and the solid was taken up again in a minimal amount of MeOH. The mixture was concentrated under vacuum to a total volume of ~20 mL at which point the unreacted Fe(OAc)$_2$ precipitates. The solid was separated by centrifugation and the mother liquor is chromatographed on a Sephadex LH-20 column (2×30 cm) using MeOH as eluent. The initial colored band was collected and Fe(III)TMPyP (OAc) was isolated by precipitation after evaporation of solvent and trituration with ether to give 85 mg (26%) of the desired product as confirmed by mass spectral analysis.

Example 2
Synthesis of 5,10,15,20-tetrakis(3,5-disulfonatedmesityl) porphyrin octasodium salt ($H_2$TMPS).

5,10,15,20-tetramesitylporphyrin ($H_2$TMP) was prepared by the condensation of pyrrole and mesitaldehyde in sealed glass tubes by the method of Badger (G. M. Badger, R. A. Jones, R. L. Laslett *Aust. J. Chem.*, 17, 1022, [1964]) or in refluxing collidine according to the literature preparation of Meunier (Meunier et. al. *Nouv. J. Chim.*, 10, 39–49, [1986]). Chlorin impurities were removed by oxidation with 2,3-dichloro-5,6-dicyano-1,4,-benzoquinone in refluxing benzene followed by chromatography on basic alumina. Both methods produced nearly identical yields of $H_2$TMPS.

Synthesis of $H_2$TMPS was achieved using a slight modification of the method of Meunier (Meunier et. al. *Inorg. Chem*, 31, 1999–2006, [1992]). A 25 mL round bottom flask equipped with a reflux condenser and stir bar was charged with $H_2$TMP (1.0 g, 1.28 mmole). Oleum ($H_2SO_4$+18–23% $SO_3$) 10 mL was added and the reaction was heated to 80° C. for 40 min. The reaction was cooled and its contents was added dropwise to 100 mL of water cooled in an ice bath. The resulting water solution was neutralized with 2N NaOH (~220 mL) to a pH=6–7. The water was removed by evaporation and the resulting solid residue was triturated with a minimal amount of MeOH. The resulting precipitate was removed by filtration and the filtrate was further concentrated to 60 mL under vacuum. The resulting precipitate (additional $Na_2SO_4$) was separated by centrifugation. The supernatant was evaporated to dryness generating 1.59 g (78%) of the desired sulfonated porphyrin.

Example 3
Synthesis of Acetato 5,10,15,20tetrakis(3,5,disulfonatomesityl)porphyrin Manganese(III) octasodium salt (Mn(III)TMPS).

$H_2$TMPS (0.2 g, 0.125 mmole) and Mn(OAc)$_2$(0.296 g, 1.71 mmole) was dissolved in 38 mL of water and was heated to 85° C. for 1 h. The reaction was monitored by visible spectroscopy and was determined to be complete when the Soret band (416 nm) of the free base porphyrin was replaced by a new band at 468 nm characteristic of Mn(III) porphyrin species. The reaction was reduced in volume under vacuum to 10 mL and was chromatographed on a Dowex 50WX-8 cation exchange resin (H$^+$form) to remove excess Mn(OAc)$_2$. The eluent was reduced in volume to 10 mL and was adjusted to pH=8.0 with 1.0 N NaOH. The resulting solution was evaporated to dryness. The residue was taken up in 7 mL of MeOH and chromatographed on a Sephadex LH-20 column using MeOH as eluent. The purple band was collected and evaporated to dryness giving 0.175 g(90%) of the desired metallated porphyrin as determined by mass spectral analysis.

Example 4
Synthesis of Acetato-5,10,15,20-tetrakis(3,5-disulfonatomesityl)porphyrin Iron (III) octasodium salt (Fe (III)TMPS).

$H_2$TMPS (0.2 g, 0.125 mmole) and Fe(OAc)$_2$ (0.300 g 1.72 mmole) was dissolved in 38 mL of water. The reaction mixture was brought to reflux and was monitored by visible spectroscopy to determine complete metallation. Upon completion the reaction was filtered and reduced in volume to 10 mL. The orange-brown reaction mixture was passed through a Dowex 50WX-8 cation exchange column (H+from) to remove excess Fe(OAc)$_2$. The eluent was reduced in volume to 10 mL and was adjusted to a pH=7.5 with 1.0 N NaOH. The resulting solution was evaporated to dryness. The residue was taken up in 7 mL of MeOH and chromatographed on a Sephadex LH-20 column using MeOH as eluent. The orange-brown band was evaporated to dryness giving 0.170 g (72%) of the desired Fe porphyin as confirmed by mass spectral analysis.

Example 5
Synthesis of Acetato-5,10,15,20-tetrakis(3,5-disulfonatomesityl)porphyrin Nickel (II) octasodium salt (Ni(II)TMPS).

$H_2$TMPS (0.1 g, 0.063 mmole) and Ni(OAc)$_2$ (0.156 g, 0.63 mmole) was dissolved in 20 mL of water and was refluxed for 3 h. The reaction mixture was orange in color indicative of the Ni porphyrin. The completion of the reaction was confirmed by Vis spectroscopy. The reaction was reduced in volume to 5 mL and chromatographed on a Dowex 50 WX-8 ion exchange column (H$^+$ form) to remove excess Ni(OAc)$_2$. The eluent was reduced in volume to 5 mL and was adjusted to a pH=8.0 with 1.0 N NaOH. The resulting solution was evaporated to dryness. The residue was taken up in 7 mL of MeOH and chromatographed on a Sephadex LH-20 column using MeOH as eluent. Product was isolated by removal of solvent to give 0.090 g (85%) of the desired metallated porphyrin as confirmed by mass spectral analysis.

Example 6
Synthesis of N,N'-ethylenebis(3,3'dimethoxysalicylideneamine) ligand.

A modification of the procedure of Coleman was used (Coleman et al. *Inorg. Chem*, 20, 700, [1981]). A 100 mL round bottom flask equipped with a stir bar was charged with 25 mL of absolute EtOH and 3-methoxysalicyladehyde (3.04 g, 0.02 mol). A 20 mL solution of absolute EtOH and ethylenediamine (0.601 g, 0.01 mol) was freshly prepared and was added in one portion to the salicylaldehyde. The reaction was refluxed for 1 h during which time a yellow-orange precipitate appeared. The product was collected by filtration, washed with 100 mL of hot ethanol, and dried under vacuum to give 4.4 g (98%) of the desired product.

Example 7
Synthesis of Chloro[N,N'-ethylenebis(3,3'-dimethoxysalicylideneaminato)iron (III)

N,N'-Ethylenebis(3,3'dimethoxysalicylideneamine) (0.05 g, 0.188 mmole) was dissolved in 20 mL of MeOH and Fe(Cl)$_3$ (0.030 g, 0.188 mmole) was added in one portion. The solution was refluxed for 1 h after which time the solvent was removed under vacuum. The purple residue was washed with a minimal amount of water. The solid was taken up in 10 mL of MeOH, filtered and re-isolated by removal of solvent to give 0.047 g (70%) of the desired iron complex.

Example 8
Synthesis of 12,14-Dimethyl-1,4,8,11-tetraazacyclotetradeca-11,13-dienatonickel(II) Hexaflorophosphate, Ni(II)([14]dienoN$_4$)PF$_6$ Ni(II)([14]dienoN$_4$)PF$_6$ was prepared by the method of Martin and Cummings (Martin, J. G.; Cummings, S. C. *Inorg. Chem.*, 12, 1477–1482, [1973]). The compound was characterized by mass spectral analysis and was shown to be consistent with the desired structure.

Example 9
Synthesis of 12,14-Dimethyl-1,4,8,11-tetraazacyclotetradeca-11,14-dienenickel(II) Hexaflorophosphate, Ni(II)([14]dieneN$_4$)(PF$_6$)$_2$ Ni(II)([14]dieneN$_4$)(PF$_6$)$_2$ Ni(II)([14]dieneN$_4$)(PF$_6$)$_2$ was prepared from Ni(II)([14]dienoN$_4$)PF$_6$ by the method of Martin and Cummings (Martin, J. G.; Cummings, S. C. *Inorg. Chem.*, 12, 1477–1482, [1973]).

Example 10
Synthesis of 6,8,15,17-Tetramethyldibenzo[b,i][1,4,8,11 tetraazatetradeca-2,4,7,9,12,14-hexaenatonickel(II), Ni(II)[14]12eneN$_4$ Ni(II)[14]12eneN$_4$ was prepared by the method of Goendken et. al. (Goendken et. al. *J.C.S. Chem.Comm.*, 337–338, [1973]). The complex was characterized by mass spectral analysis and which was consistent with the desired structure.

Example 11
This example describes the preparation of peroxynitrite stock solutions used in these studies. A modified version of the procedure described by Hughs was used (Hughs, M. N.; Nicklin, H. G. *J. Chem. Soc.*, (A), 450–452, [1968]).

To 10 mL of vigorously stirred 0.6 M NaNO$_2$ solution maintained at 0° C. was added an equal volume of a HCl/H$_2$O$_2$ solution (0.6 M HCl and 0.7 M H$_2$O$_2$) followed immediately by the rapid addition of 10 mL of 0.75 M NaOH. The resulting yellow solution was treated with 25 mg of MnO$_2$ for 3 min. and was immediately filtered. The filtrate was placed in a −20° C. freezer for several days which resulted in the fractionation of the sodium peroxynitrite as evident by a fine yellow band visible at the top of the flask. The yellow band was collected to yield ~1 mL of a 280 mM sodium peroxynitrite solution. This solution could be stirred frozen at −20° C. for several days with minimal decomposition of peroxynitrite.

Example 12
This example describes the procedures used to determine if compounds are peroxynitrite decomposition catalyst by stopped-flow kinetic analysis.

All analysis were run using potassium phosphate buffers (Calbiochem) which were biological grade using ultra pure water prepared by the method of Riley (Riley, D. P. et. al. *Anal. Biochem.* 196, 344–349, [1991]). Kinetic measurements were made on an OLIS Rapid Scanning Stopped-Flow Spectrometer (On-Line Instrument Systems Inc., Bogart, Ga.)) using the OLISRSM-1000 Operating system for data acquisition and manipulation. Peroxynitrite has a strong absorbance at 302 nm (extinction coefficient =1670 M−1 cm−1) and has been shown to decompose in a process that is first-order in sodium peroxynitrite and first order in protons (Hughs, M. N.; Nicklin, H. G. *J. Chem. Soc.*, (A), 450–452, [1968]) with $t_{1/2}$=1.9 sec. at 37° C pH=7.4 (Beckman, J. S. et.al. *Proc. Natl. Acad. Sci. USA*, 87, 1620–1624, [1990]).

Thus, in a typical experiment the natural background decomposition rate of sodium peroxynitrite was determined as follows. A 24 mM stock solution of sodium peroxynitrite in 50 mM NaOH is load into the small volume syringe and 100 mM potassium phosphate pH=7.4 is charged into the large volume syringe of the stopped-flow spectrophotometer. All stopped -flow measurements were made at 22 ° C. Injection of the solutions into the sample compartment results in ~25 fold dilution of the stock sodium peroxynitrite. The decomposition of sodium peroxynitrite is first order in peroxynitrite with a $t_{1/2}$=5.2 see and a $k_{obs}$=1.39×10$^{-1}$±0.15 sec$^{-1}$. To test for catalytic peroxynitrite decomposition activity, the metal complex was dissolved in 100 mM potassium phosphate buffer pH=7.4 and loaded into the large syringe and the decomposition of peroxynitrite was monitored as described above. The catalytic rate constant ($k_{cat}$ M-1 sec$^{-1}$) for the complexes tested was determined by varying the complex concentration and plotting $k_{obs}$ vs [complex] Table 1. The $k_{obs}$ were obtained from averages of three stopped flow analysis at each catalyst concentration. Data representative of this analysis for a variety of compounds is shown in FIG. 1. The simple di and trivalent chloride salts of Mn, Fe, Co, Cu, and Ni showed no catalytic peroxynitrite decomposition activity at concentration of 0.050 mM and below.

TABLE 1

CATALYTIC RATE CONSTANTS FOR THE DECOMPOSITION OF SODIUM PEROXYNITRITE BY METAL COMPLEXES AT pH = 7.4 AND 22° C.

| Example No. | Complex | $k_{cat}$ (M$^{-1}$ sec$^{-1}$) |
|---|---|---|
| 1 | Fe(III)TMPyP | 2.75 × 10$^{+6}$ |
|  | Fe(III)TPPS | 2.06 × 10$^{+6}$ |
| 4 | Fe(III)TMPS | 1.60 × 10$^{+5}$ |
| 5 | Ni(II)TMPS | 8.72 × 10$^{+4}$ |
| 7 | Fe(III)(3,3'MeO$_2$Salen) | 5.00 × 10$^{+4}$ |
| 3 | Mn(III)TMPS | 2.90 × 10$^{+4}$ |
| 8 | Ni(II)([14]dienoN$_4$)PF$_6$ | 2.05 × 10$^{+4}$ |
| 9 | Ni(II)([14]dieneN$_4$)(PF$_6$)$_2$ | 1.80 × 10$^{+4}$ |
| 10 | Ni(II)[14]12eneN$_4$ | 1.70 × 10$^{+4}$ |
|  | Fe(III)EDTA | 2.00 × 10$^{+4}$ |
|  | Fe(III)Citrate | 1.50 × 10$^{+4}$ |
| 2 | H2TMPS | Inactive |
| 1(SM)[b] | H2TMPyP | Inactive |
|  | ZnTMPyP | Inactive |
|  | Ni(CR)Cl$_2$[a] | Inactive |

[a]CR = 2,12-dimethyl-3,7,11,17-tetraazabicyclo[11.3.1]heptadeca-1(17),2,11,13,15-pentaene
[b]Starting material Example 13

This example illustrates the inactivation of CuZn-superoxide dismutase (CuZnSOD) by peroxynitrite and that peroxynitrite decomposition catalyst shown to be active in Example 12 protect CuZnSOD against inactivation by peroxynitrite.

Stock solutions of bovine liver CuZnSOD (DDI Pharmaceuticals Inc., Mountain View CA) were prepared by dissolving -1.0 mg of enzyme in 10 mL of 50 mM potassium phosphate buffer at a pH=7.4. The activity of this solution to dismutate superoxide was determined by the method of Riley (Riley, D. P. et. al. *Anal. Biochem.* 196, 344–349, [1991]). All $k_{obs}$ were the average of triplicate runs using a stopped flow spectrophotometer manufactured by Kinetic Instruments Inc. (Ann Arbor, Mich.) and was interfaced to a MAC IICX personal computer.

Inactivation of CuZn SOD by peroxynitrite.

Inactivation of peroxynitrite was performed by aloquating 1.0 mL of stock CuZn SOD solution into 50 mM potassium phosphate buffer pH=7.4 such that a final assay volume of 10 mL is achieved after addition of peroxynitrite and EDTA solutions. To these assay solution was added various amounts of peroxynitrite (25 mM stock solution) such that the final concentration of peroxynitrite in the assay varied from 0, 25, 50, 75 and 100 uM. After the addition of peroxynitrite, 100 uL of a 2.5 mM stock EDTA solution was added to each assay solution such that the final concentration of EDTA was 250 uM. Each solution was then assayed by stopped flow analysis for superoxide dismutase activity. A plot of $k_{obs}$ vs peroxynitrite concentration is shown in FIG. 2. Control reaction which contained CuZnSOD in the presence of 250 uM EDTA alone and 100 uM potassium nitrite or nitrate showed no decrease in CuZnSOD activity.

Example 14

Protection of CuZnSOD from inactivation by peroxynitrite using peroxynitrite decomposition catalysts Assay solutions were prepared as described above except for the addition of various of peroxynitrite decomposition catalyst. The final solution volume was maintained at 10 mL. Thus, to the assay solutions Fe(III)TMPyP (0.5 and 1.0 uM final concentration) and Fe(III)TMPS (1.0 and 5.0 uM final concentration) was added. The solution were then treated with various amounts of peroxynitrite such that the final concentrations of 0,25, 50, 75 and 100 uM were achieved. Following treatment with peroxynitrite EDTA was added to a final concentration of 250 uM. The solutions were then assayed for SOD activity. Plots of $k_{obs}$ vs [peroxynitrite] at various catalysts concentrations illustrates the protective effect of Fe(III)TMPyP FIG. 3 and Fe(III)TMPS FIG. 4. Under the assay conditions employed, Fe(III)TMPyP and Fe(II)TMPS were shown not to be effective catalysts for the dismutation of superoxide.

Example 15

In Vitro Evaluation:

Serials: Human recombinant tumor necrosis factor-alpha (TNF-a) was obtained from Genzyme Corporation, Cambridge, MA. Human recombinant complement C5a and L-arginine (L-arg) was purchased from Sigma Chemical Company, St. Louis, Mo. Authentic peroxynitrite in 50 mM NaOH was prepared as described above.

Isolation of Endothelial Cells: Human dermal microvascular endothelial cells (HDME cells) from neonatal foreskin were prepared as previously described (Marks, R. M., Czerniecki, M., and Penny, R. *In Vit. Cell. Devel. Biol.*, 21, 627–635 [1985]). In brief, neonatal foreskin tissue from several donors was washed in 70% ethanol, cut into small pieces, then emersed in trypsin (0.6%; Irvine Scientific, Santa Ana, Calif.) and EDTA (1%; Sigma Chemical Company, St. Louis, Mo.) for 7–9 minutes. The endothelial cells were removed by pressing the unkeratinized surface of the tissue with a scalpel blade. The cells were centrifuged through a 35% Percoll density gradient (Sigma Chemical Company, St. Louis, Mo.). After centrifugation at 250×g for 10 min, cells corresponding to a density of less than 1.048 g/ml were collected and plated onto gelatin coated tissue culture dishes (0.1%; Sigma Chemical Company, St. Louis, Mo.). Contaminating cells were weeded daily using a 25 gauge needle mounted onto a tuberculin syringe. Purified endothelial cells were grown to passage 5 (~8 population doublings) in MCDB 131 (Endothelial basal medium; Clonetics Corporation) supplemented with 30% human serum (BioWittaker, Inc., Walkersville, Md.), 10 ng/ml EGF (Collaborative Biomedical Products, Bedford, Mass.), 2 mM L-glutamine (Irvine Scientific, Santa Ana, Calif.), and 250 µg/ml dibutyryl CAMP, 1 µg/ml hydrocortisone (Sigma Chemical Company, St. Louis, Mo.). These cells were characterized as normal endothelial cells by testing for endothelial cell markers (Factor VIII immunoreactivity, cell-associated angiotensin converting enzyme activity, and low density lipoprotein uptake). Cells were cryopreserved at passage 5 in 10% DMSO for use in the subsequent assays after testing negative for mycoplasma (Coriel Institute, Camden, N.J.).

Preparation of Neutrophils: Human neutrophils were isolated from peripheral blood of healthy donors (Look, D. C., Rapp, S. R., Keller, B. T., and Holtzman, M. J. *Am. J. Physiol.*, 263, L79–L87 [1992]). EDTA anti-coagulated blood was separated using a single-step density centrifugation (PMN Prep, Robbins Scientific, Sunnyvale, Calif.) followed by several washes in Hank's buffered saline solution (HBSS; Sigma Chemical Company, St. Louis, Mo.) and hypotonic lysis of erythrocytes. Preparations contained >95% neutrophils and were >95% viable by trypan blue (GIBCO Laboratories, Grand Island N.Y.) exclusion. Purified neutrophils were suspended in HBSS supplemented with 0.01% BSA (Miles, Inc., Kankakee, Ill.) and 300 uM L-arg (HBSSBA) at a concentration of $5 \times 10^6$ cells/ml.

Endothelial Cell Injury Assays: The cytotoxic effects of stimulated neutrophils or peroxynitrite on endothelial cells was determined using a $^{51}$Cr-release assay as described by Moldow (Moldow et. al. *Methods Enzymol.*, 105, 378–385, [1984]). Passage 5 HDME cells were grown to a density of $\sim 1-2 \times 10^4$ cells/cm$^2$ (~90% confluence) in 96 well microtiter plates and labeled for 18 h with 10 uCi/ml sodium [$^{51}$Cr] chromate (Amersham Corporation, Arlington Heights, Ill.). The HDME cells were cytokine-activated for 4 h with 100 U/ml human recombinant tumor necrosis factor-alpha (TNF-a; Genzyme Corporation, Cambridge, Mass.), then washed twice with HBSSBA. Suspensions of neutrophils were added at a concentration of $2.5 \times 10^5$/well and allowed to settle for 15 min. Unless otherwise noted, the neutrophils were activated by priming with 25 U/ml TNF-a for 10 min followed by activation with 3 µg/ml complement component C5a (Sigma Chemical Company, St. Louis, Mo.). Incubations were continued for 2 h at 37° C. When authentic peroxynitrite was used, it was added in the absence of neutrophils. Peroxynitrite was added directly to the HDME cell layer from a 25 mM stock in 50 mM NaOH giving a final concentration from 0–800 uM. All inhibitors were made fresh immediately prior to the assay in HBSSBA and added as 1/10 of the well volume before peroxynitrite addition or neutrophil activation.

$^{51}$Cr release was determined by aspiration of the supernatant from each well (soluble fraction). The monolayers were washed gently with HBSSBA to remove non-adherent cells and the washes pooled with the soluble fraction. The adherent cells from each well were solubilized with 1 N NaOH and removed to a separate tube. Both fractions were analyzed by gamma scintillation spectrometry. Results were expressed as percent $^{51}$Cr release as follows: % release=cpm (soluble+nonadherent/total cpm per well)×100. Specific cytotoxicity reflects the difference between $^{51}$Cr release induced by stimulated neutrophils and unstimulated neutrophils (typically 1–2% above spontaneous release). Results were confirmed in 2–3 separate assays and the data presented are representative.

As can be seen from FIG. 5, addition of peroxynitrite to endothelial cells results in a dose dependent increase in cell injury demonstrating the cytotoxic effects of peroxynitrite. Complexes which have been shown to be peroxynitrite decomposition catalysts by stopped flow analysis are capable of protecting against peroxynitrite mediated cell injury FIG. 6. These complexes are also capable of protecting against neutrophil mediated cell injury in a dose dependant fashion FIG. 7.

Example 16

Protocol for Cell Protection Assays using Peroxynitrite Decomposition Catalysts: A cell viability assay was established to rapidly assess the efficacy of peroxynitrite(PN) catalysts in protecting cells from PN25 mediated injury and death. The peroxynitrite challenge consisted of a pulse of synthetic PN added exogenously to cells. In order to better assess the efficacy of PN catalysts in protecting cells from PN-mediated damage, a quantity of peroxynitrite(in 50 mM NaOH) determined to cause maximal injury(100%) was added as an exogenous pulse to each well of cells in the presence or absence of catalyst. The NaOH vehicle was not toxic by itself.

Cells(RAW 264.7 cells or P815 mastocytoma cells; American Type Culture Collection, Rockville, Md.) were plated to confluence on 96-well tissue culture plates. Each well is washed twice with Dulbecco's phosphate buffered saline(DPBS; GIBCO BRL, Grand Island, N.Y.) to remove protein and other serum components which might react with the exogenous peroxynitrite. To each well is then added 200 µl of DPBS. PN is next placed into separate wells at increasing concentrations and cell viability monitored. The dose at which maximal cell death is attained is then utilized for the catalyst protection assessment.

Phosphate-buffered saline (200 uL) containing increasing concentrations of catalyst is next placed into individual wells of cells. The maximal dose of PN is subsequently administered to all wells of cells. After 15 minutes, the medium is removed from each well and the cells are either allowed to recover overnight in Earles minimum essential medium without phenol red and supplemented with 10% fetal bovine serum or alternatively the plate of cells is assayed that day for mitochondrial integrity using the Alamar Blue viability assay(Alamar Biosciences, Inc.; Sacramento, Calif.). In either case, cells are incubated at 37° C. in 5% $CO_2$.

Cell injury is measured as follows. Briefly, 10% Alamar Blue(v/v) in Earles MEM with 10% FBS is added to each well of cells for 1–2h. Cell metabolism of the dye generates a fluorescent product which is directly related to the number of viable cells. Moreover, the production of the fluorescent metabolite is linear for over 2 h. The amount of fluorescent product in 100 µl of conditioned medium from each well of cells is then measured with an IDEXX fluorescent plate reader (gain setting of 1%) at an emission wavelength of 575 nm after exciting at 545 nm. Viability is either given as absolute fluorescent units or as a percent of the value obtained for untreated cells(100%).

As can be seen in FIG. 8, both Fe- and Ni- coordinated catalysts were able to protect the murine monocyte-macrophage line RAW 264.7; in this experiment PN was added at a dose causing a 50% decrease in cell viability.

Comparison of increasing PN doses on RAW and P815 cells showed no evidence for a differential susceptibility to peroxynitrite-mediated injury(data not shown). However, as shown in FIG. 9, there is a significant protection of cells by Fe-TMPyP, FeTMPS, and FeTPPS while H$_2$TMPyP and ZnTMPyP were relatively ineffective (data not shown), a result consistent with their lack of catalytic potency. Addition of catalyst after PN was unable to rescue the cells from injury (data not shown) indicating the ability of the catalysts to protect cells directly from oxidative damage due to PN.

Example 17

In vivo Evaluation:

Carrageenan-induced paw edema. The effects of peroxynitrite catalysts in vivo were initially tested on the carrageenan-induced paw edema. The choice of using this in vivo model of inflammation was based on the knowledge that 1) the inflammatory response is blocked by NOS inhibitors and 2) by superoxide dismutase (SOD). This indicates the participation of both NO and of O$_{2-}$. Male Sprague Dawley rats were purchased from Harlan Sprague-Dawley (Indianapolis, Ind.). Male Sprague Dawley rats (175–200 g) received a subplantar injection in the right hind paw of carrageenan (0.1 ml of a 1% suspension in 0.85% saline). Paw volume was measured by a plethysmometer immediately before the injection of carrageenan and then at hourly intervals from 1 to 6 h. Edema was expressed as the increase in paw volume (in ml) measured after carrageenan injection compared to the pre-injection value for individual animals.

Rats were given a bolus i.v. injection of active or inactive peroxynitrite catalysts 1 hour after the intraplantar injection of carrageenan; paw swelling was assessed thereafter every hour for up to 6 h. The relative % inhibition obtained with these agents is summarized in Table 2. Under these experimental conditions the inactive peroxynitrite catalysts H$_2$TMPS, ZnTMPyP or MnTPPS (all given at 30 mg/kg) or FeCl$_3$ (5 mg/kg, n=6) failed to inhibit edema formation.

TABLE 2

% Inhibition of Paw Edema by Peroxynitrite Decomposition Catalysts

| Compound | Dose(mg/kg) | Time (h) Post Carrageenan | | | | | |
|---|---|---|---|---|---|---|---|
| | | 1 | 2 | 3 | 4 | 5 | 6 |
| FeTMPS | 3 | 0 | 42 | 47 | 47 | 33 | 33 |
| | 10 | 0 | 61 | 60 | 53 | 53 | 47 |
| | 30 | 0 | 85 | 80 | 80 | 80 | 81 |
| FeTMPy | 3 | 0 | 9 | 10 | 17 | 6 | 0 |
| | 10 | 6 | 13 | 11 | 28 | 21 | 2 |
| | 30 | 0 | 44 | 43 | 50 | 32 | 32 |
| FeTPPS | 3 | 0 | 29 | 20 | 20 | 19 | 5 |
| | 10 | 0 | 17 | 20 | 23 | 19 | 20 |
| | 30 | 0 | 27 | 25 | 30 | 34 | 33 |
| ZnTMPS | 30 | 0 | 0 | 0 | 0 | 0 | 0 |
| H$_2$TMPS | 30 | 0 | 0 | 0 | 0 | 0 | 0 |
| MnTMPS | 30 | 0 | 0 | 0 | 0 | 0 | 0 |

Results are expressed as % inhibition of paw edema when compared to values obtained in control rats at the same time points. Each point is the mean ± s.e.m for n = 6 animals.

Induction of intestinal damage by endotoxin in the rat: Multiple organ failure syndrome (MOFS) that develops following the septic attack is in most cases fatal. The "motor" of MOFS is the gastrointestinal tract, in particular the small intestine. Extensive ischaemia may be found in the intestinal mucosa due to profound vasoconstriction. Ischaemia and hypoxia result in mucous lesions, found both in animals (rat, cat, dogs) and humans. The origin of the mucous lesion is hypoxia. During reperfusion (e.g, after the initial severe vasoconstriction), O$_{2-}$ may be liberated and play an important role in the pathogensis of mucous lesions in the GI tract. Intestinal damage that results from shock induced by sphlanchnic artery occlusion is prevented by superoxide dismutase and LPS induced intestinal inflammation is inhibited by non-selective inhibitors of the nitric oxide pathway (Boughton-Smith, N. K et al., 1993). There is now substantial experimental and clinical evidence that suggests that excessive NO production has an important pathological role in the hypotension, hyporesponsiveness to vasoconstictors and the cardiovascular collapse associated with septic shock. Furthermore, nitric oxide synthase inhibitors prevent against the intestinal damage caused by endotoxin. We have developed a model of intestinal injury in rats by endotoxin and assessed the effects of therapeutic administration of peroxynitrite catalysts.

Intestinal vascular permeability was determined as the leakage into the jejunal tissue of [$^{125}$I]-labelled bovine serum albumin ([$^{125}$I]-BSA) administered intravenously (0.5 ml; 0.5 μCi) together with either LPS (3 mg/kg, serotype O111:B4) or isotonic saline. At 4 h after LPS administration, segments of jejunal tissue were ligated and removed. The intestinal tissues were rapidly washed, blotted dry and weighed. Blood (0.5 ml) was collected into tubes containing tri-sodium citrate (0.318% final concentration) and plasma prepared by centrifugation (10,000 g×10 min). The {$^{125}$I}-BSA content in segments of whole tissue and in aliquots of plasma (100 μl) was determined in a gamma counter. The total content of plasma in the intestinal tissues was expressed as μl/g tissue. Changes in intravascular volume in the intestinal tissue was determined in an additional group of rats by administering ([$^{125}$I]-BSA) intravenously 2 min before removal of the jejunum. The tissue and plasma content of radiolabel was determined and intravascular volume expressed as μl/g tissue. This value was substracted from that obtained in the plasma leakage studies to obtain a measure of the intestinal plasma albumin leakage. After LPS administration (4 h), there was a significant (P<0.01) increase in the plasma leakage (from 77±10 to 224±18 μl/g tissue, n=8). Administration of FeTMPS or FeTMPyP (30 mg/kg, i.v, n=4), 3 h after LPS injection, caused a reduction in radiolabelled albumin leakage determined 1 h later, as shown in FIG. 10. In contrast, administration of the inactive peroxynitrite catalyst ZnTMPyP (30 mg/kg, i.v, n=4), 3 h after LPS injection, did not inhibit radiolabelled albumin leakage determined 1 h later (FIG. 10). This data was supported by histological examination of the jejunal tissues. When compared to saline treated rats, LPS evoked profound jejunal damage with severe disruption of plicae and villi. LPS-induced damage was less severe in jejunums taken from rats treated with FeTMPS or FeTMPyP (30 mg/kg, i.v.).

Thus, the compounds which are compounds or complexes of the present invention are novel and can be utilized to treat numerous inflammatory disease states and disorders. For example, reperfusion injury to an ischemic organ, e.g., reperfusion injury to the ischemic myocardium, inflammatory bowel disease, rheumatoid arthritis, osteoarthritis, hypertension, psoriasis, organ transplant rejections, organ preservation, impotence, radiation-induced injury, asthma, atherosclerosis, thrombosis, platelet aggregation, side effects from drug treatment of cancer metastasis, influenza, stroke, burns, trauma, acute pancreatitis, pyelonephritis, hepatitis, autoimmune diseases, insulin-dependent diabetes mellitus, disseminated intravascular coagulation, fatty embolism, adult and infantile respiratory distress, and hemorrhages in neonates.

Patients receiving IL-2 therapy often develop potentially life-threatening side effects that include fever, chills, hypotension, capillary leak syndrome, as well as evidence of multiple organ dysfunction, specifically including renal insufficiency and cholestatic jaundice. IL-2 induces a complex network of cytokines that include tumor necrosis factor, interleukin 1 and 6. Therefore, IL-2-treated patients resemble patients with endotoxemia (hypotension, elevated TNF levels, elevated cytokine levels etc). Some of these induce release of free radicals as well as inducing iNOS with subsequent release of NO. A recent paper shows that iNOS is induced in patients that receive IL-2 for treatment of renal cell carcinoma and malignant melanoma (Hibbs, J. B. et al., Evidence for cytokine-inducible nitric oxide synthesis from L-arginine in patients receiving interleukin-2 therapy. J. Clin. Invest. Vol 89, 867–877).

Activity of the compounds or complexes of the present invention for protecting superoxide dismutase can be demonstrated using the stopped-flow kinetic described above. Stopped-flow kinetic analysis is an accurate and direct method for quantitatively monitoring the decay rates of peroxynitrite in water. The stopped-flow kinetic analysis is suitable for screening complexes for catalytic peroxynitrite decomposition activity and active complexes of the present invention, as identified by stopped-flow analysis, are shown to correlate to treating the above disease states and disorders.

In other words, the present invention is for the methods and compositions for the treatment of a disease or condition advantageously affected by decomposition of peroxynitrite which is accelerated over a natural background rate of decay, preferably in humans suffering from such disease or condition, which comprises administering a metal complex, in dosage unit form, of accelerated-rate-effective amounts for decomposing peroxynitrite preferably wherein the metal complex is as defined above. Such methods or compositions accomplish the treatment of these diseases without disadvantageously affecting normal biologically advantageous mechanisms.

Total daily dose administered to a host in single or divided doses may be in amounts, for example, from about 1 to about 100 mg/kg body weight daily and more usually about 3 to 30 mg/kg. Dosage unit compositions may contain such amounts of submultiples thereof to make up the daily dose. The number of submultiples is preferably about one to three times per day of about 30 mg/kg per unit dosage form. The serum concentrations of the doses are about 15 $\mu$M to 1.5 mM with preferred ranges of 3 to 300 $\mu$M.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, granules and gels. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more compounds of the present invention or with one or more compounds which are known to be effective against the specific disease state that one is targeting for treatment.

We claim:

1. A method of treating a medical condition which is advantageously affected by the accelerated decomposition of peroxynitrite in a subject having such condition comprising administering to the subject a metal complex which is a peroxynitrite decomposition catalyst.

2. A method of claim 1 wherein the disease is ischemic reperfusion, a side effects from drug treatment of cancer, inflammation, sepsis, stroke, multiple sclerosis or parkinson's disease.

3. A method of claim 2 wherein the disease-or condition is acute or chronic inflammation.

4. A method of claim 2 wherein the disease is sepsis.

5. A method of claim 2 wherein the disease is stroke.

6. A method of claim 2 wherein the disease is ischemic reperfusion.

7. A method of claim 1 wherein the compound is a ligand structure of a metal which is selected from the group consisting of Mn, Fe, Ni and V.

8. A method of claim 7 wherein the ligand is a macrocyclic with a metal which is Mn, Fe or Ni.

9. A method of claim 4 wherein the ligand is a porphyrin containing metal.

10. A pharmaceutical composition in dosage unit form for the treatment of a disease in humans advantageously affected by decomposition of peroxynitrite at a rate over the natural background rate of decay of peroxynitrite in humans suffering from the disease comprising, per dosage unit, an amount of a metal complex effective for the decomposition of peroxynitrite.

11. A method of claim 1 wherein the metal complex is of the formula

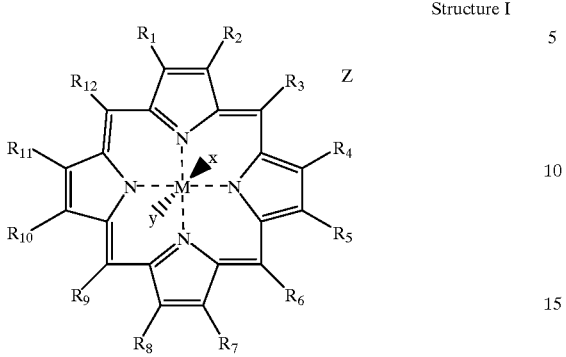

Structure I wherein
$R_3$, $R_6$, $R_9$ or $R_{12}$ are independently selected a group consisting of H, alkyl, alkenyl, $CH_2COOH$, phenyl, pyridinyl, and N-alkylpyridyl such that phenyl, pyridinyl and N-alkylpyridyl are

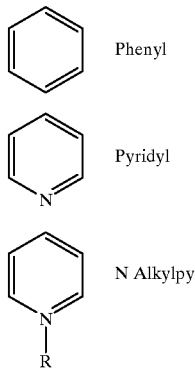

Phenyl

Pyridyl

N Alkylpyridine which are attached at a carbon atom, and
wherein
phenyl is optionally substituted by halogen, alkyl, aryl, benzyl, COOH, $CONH_2$, $SO_3H$, $NO_2$, $NH_2$, $N(R)_{3+}$, NHCOR' wherein R is hydrogen, alkyl, aryl, alkaryl and R' is alkyl;
pyridinyl is optionally substituted by halogen, alkyl, aryl, benzyl, COOH $CONH_2$, $SO_3H$, $NO_2$, NH2, $N(R)_{3+}$, or NHCOR' wherein R and R' are as defined above; and
N-alkylpyridine ring is optionally substituted by halogen, alkyl, aryl, benzyl, COOH, $CONH_2$, $SO_3H$, $NO_2$, $NH_2$, $N(R)_{3+}$ or NHCOR' wherein R and R' are as defined above;
$R_1$, $R_2$, $R_4$, $R_5$, $R_7$, $R_9$, $R_{10}$, or $R_{11}$ are independently selected a group consisting of H, alkyl, alkenyl, carboxyalkyl, Cl, Br, F, $NO_2$, hydroxyalkyl, and $SO_3H$ or $R_1R_2$ can be taken together to form a ring of from 5 to 8 carbons;
X and Y are ligands or charge-neutralizing anions which are derived from any monodentate or polydentate coordinating ligand or ligand system or the corresponding anion thereof and are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl, amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkyl aryl thiocarbamate, alkyl dithiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroanitmonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins; with the proviso that when the X and Y containing complex has a net positive charge then Z is a counter ion which is independently X or Y, or when the X and Y containing complex has net negative charge then Z is a counter ion selected from a group consisting of alkaline and alkaline earth cations, organic cations such as alkyl or alkylaryl ammonium cations; and
M is selected from the group consisting of Mn, Fe, Ni and V;

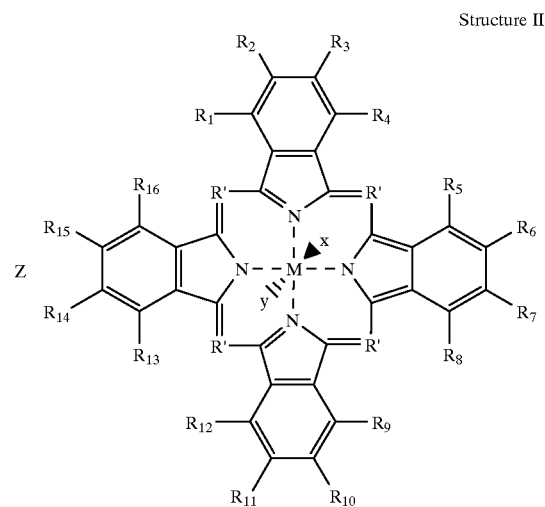

Structure II wherein
R' is CH or N;

$R_2$, $R_2'$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are independently selected from a group consisting of H, $SO_3H$, COOH, $NO_2$, $NH_2$, and N-alkylamino;

X, Y, Z and M are as defined above;

Structure III

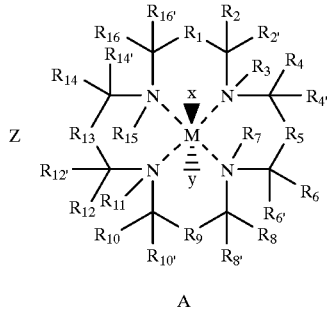

A wherein
  $R_1$, $R_5$, $R_9$, and $R_{13}$ are independently a direct bond or $CH_2$;
  $R_2$, $R_2'$, $R_4$, $R_4'$, $R_6$, $R_6'$, $R_8$, $R_8'$, $R_{10}$, $R_{10}'$, $R_{12}$, $R_{12}'$, $R_{14}$, $R_{14}'$, $R_{16}$, $R_{16}'$ are independently H or alkyl;
  $R_3$, $R_7$, $R_{11}$, $R_{15}$ are independently H or alkyl;
  X, Y, Z and M are as defined above;

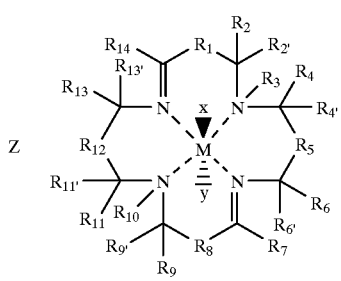

B wherein
  $R_1$, $R_5$, $R_8$, and $R_{12}$ are independently a direct bond or $CH_2$;
  $R_2$, $R_2'$, $R_4$, $R_4'$, $R_6$, $R_6'$, $R_7$, $R_9$, $R_9'$, $R_{11}$, $R_{11}'$, $R_{13}$, $R_{13}'$, $R_{14}$ are independently H or alkyl;
  $R_3$ and $R_{10}$ are independently H or alkyl;
  X, Y, Z and M are as defined above;

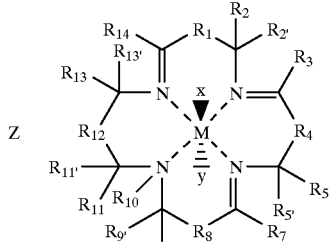

C wherein
  $R_1$, $R_4$, $R_8$, $R_{12}$ are independently a direct bond or $CH_2$;
  $R_2$, $R_2'$, $R_3$, $R_5$, $R_5'$, $R_7$, $R_7'$, $R_{11}$, $R_{11}'$, $R_{13}$, $R_{13}'$, $R_{14}$ are independently H or alkyl;

$R_{10}$ is H or alkyl;
X, Y, Z and M are as defined above;

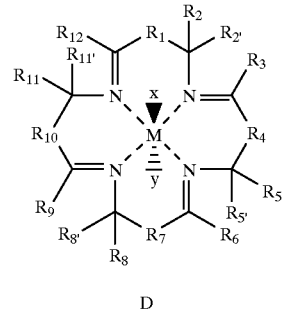

D wherein
  $R_1$, $R_4$, $R_7$ and $R_{10}$ are independently a direct bond or $CH_2$;
  $R_2$, $R_2'$, $R_3$, $R_5$, $R_5'$, $R_6$, $R_8$, $R_8'$, $R_9$, $R_{11}$, $R_{11}'$ and $R_{12}$ are independently H or alkyl;
  X, Y, Z and M are as defined above;

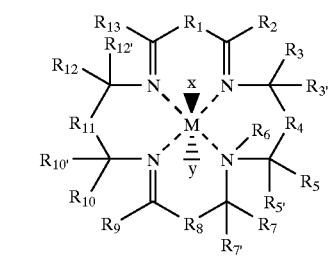

E wherein
  $R_1$, $R_4$, $R_8$ and $R_{11}$ are independently a direct bond or CH2;
  $R_2$, $R_3$, $R_3'$, $R_5$, $R_5'$, $R_7$, $R_7'$, $R_9$, $R_{10}$, $R_{10}'$, $R_{12}$, $R_{12}'$ and $R_{13}$ are independently H or alkyl;
  $R_6$ is hydrogen or alkyl;
  X, Y, Z and M are as defined above;

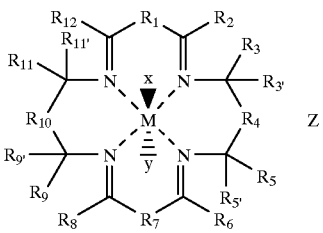

F wherein
  $R_1$, $R_4$, $R_7$ and $R_{10}$ are independently H or alkyl;
  $R_2$, $R_3$, $R_3'$, $R_5$, $R_5'$, $R_6$, $R_8$, $R_9$, $R_9'$, $R_{11}$, $R_{11}'$ and $R_{12}$ are independently H or alkyl;

X, Y, Z and M are as defined above;

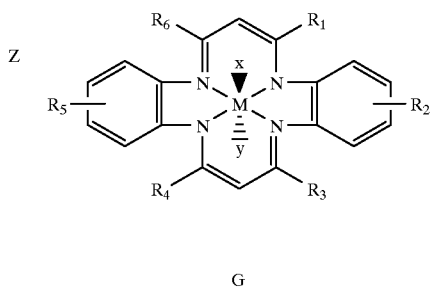

G wherein
  $R_1$, $R_3$, $R_4$ and $R_6$ are independently H or alkyl;
  R2 and 5 are independently selected from the group consisting of H, alkyl, $SO_3H$, $NO_2$, $NH_2$, halogen, COOH, $N(R)_{3+}$ wherein R is as defined above;
  X, Y, Z and M are as defined above;

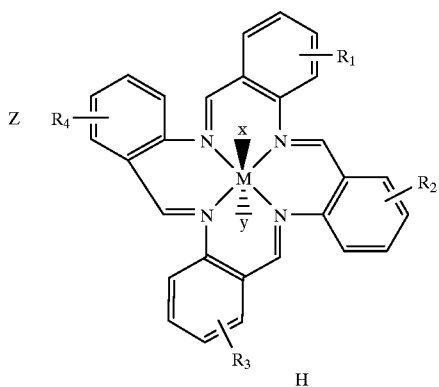

H wherein
  $R_1$, $R_2$, $R_3$, $R_4$ are independently selected from the group consisting of H, alkyl, $SO_3H$, $NO_2$, $NH_2$, halogen, COOH and $N(R)_{3+}$ wherein R is as defined above;
  X, Y, Z and M are as defined above;

Structure IV

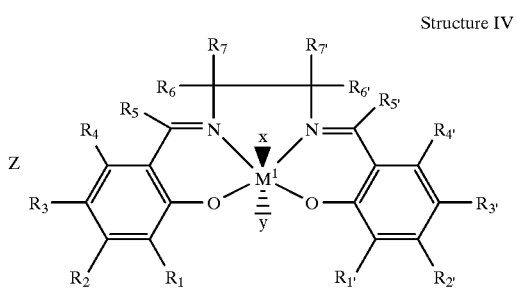

wherein
  R1, R1', R2, R2', R3, R3', R4, R4', R5, R5', R6, R6', R7 and R7' are independently selected from a group consisting of H, alkyl, alkoxy, $NO_2$, aryl, halogen, $NH_2$, $SO_3H$, and $R_6$, $R_6'$, $R_7$ and $R_7'$ may each be taken together with one other of $R_6$, $R_6'$, $R_7$ and $R_7'$ to form a cyclic group, preferably a 6 carbon cycloalkyl group;
  $M^1$ is Fe, Ni or V;
  X, Y and Z are as defined above.

12. A method of claim 11 wherein the metal complex is structure I of the formula

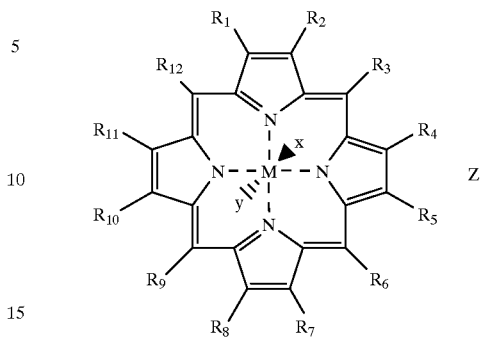

wherein $R_1$, $R_2$, $R_3$, $R_4$, $R_5$, $R_6$, $R_7$, $R_8$, $R_9$, $R_{10}$, $R_{11}$, $R_{12}$, M, X, Y and Z are as defined for Structure I in claim 11.

13. A method of claim 11 wherein the metal complex is structure II of the formula

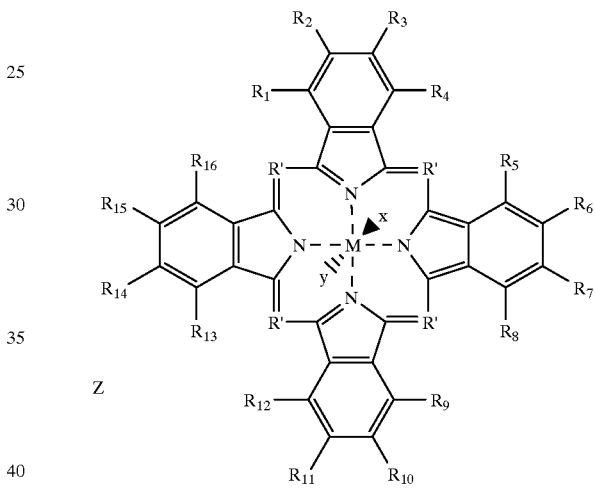

wherein R1, R2, R3, R4, R5, R6, R7, R8, R9, R10, R11, R12, R13, R14, X, Y, M and Z are as defined for Structure II in claim 10.

14. A method of claim 11 wherein the metal complex is Structure III A, IIIB, IIIC, IIID, IIIE, or IIIF of the formula as defined above.

15. A method of claim 11 wherein the metal complex is Structure IIIG or IIIH of the formula as defined above.

16. A method of claim 11 wherein the metal complex is Structure IV of the formula

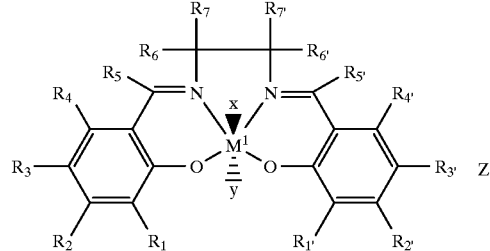

wherein
  $R_1$, $R_1'$, $R_2$, $R_2'$, $R_3$, $R_3'$, $R_4$, $R_4'$, $R_5$, $R_5'$, $R_6$, $R_6'$, $R_7$, $R_7'$, X, Y, Z and $M^1$ are as defined above.

17. A method of claim 11 wherein M is Fe.
18. A method of claim 11 wherein M is Ni.
19. A method of claim 11 wherein M is V.
20. A method of claim 11 wherein M and $M^1$ are Mn.
21. A method of claim 12 wherein M is Fe.
22. A pharmaceutical composition in dosage unit form for the treatment of a disease in humans advantageously affected by decomposition of peroxynitrite at a rate over the natural background rate of decay of peroxynitrite in humans suffering from the disease comprising, per dosage unit, an effective amount of a metal complex for the decomposition of peroxynitrite wherein the metal complex is as defined in claim 11.

* * * * *